(12) United States Patent
Forsberg et al.

(10) Patent No.: US 6,290,680 B1
(45) Date of Patent: Sep. 18, 2001

(54) PREFILLED AMPOULES AND MANUFACTURE THEREOF

(75) Inventors: Mikael Forsberg, Ekerö ; Birger Hjertman, Vällingby, both of (SE)

(73) Assignee: Pharmacia AB, Stockholm (SE)

( * ) Notice: Subject to any disclaimer, the term of this patent is extended or adjusted under 35 U.S.C. 154(b) by 0 days.

(21) Appl. No.: 09/158,273

(22) Filed: Sep. 22, 1998

Related U.S. Application Data

(60) Provisional application No. 60/061,399, filed on Oct. 6, 1997.

(30) Foreign Application Priority Data

Sep. 23, 1997 (SE) .................................................. 9703425

(51) Int. Cl.⁷ ..................................................... A61M 5/00
(52) U.S. Cl. .............................. 604/232; 211/74; 141/237
(58) Field of Search ..................................... 604/197, 232; 206/514, 528, 538, 560; 211/74, 85.13; 141/18, 21, 25–27, 237

(56) References Cited

U.S. PATENT DOCUMENTS

| 581,847 | * | 5/1897 | Carvin . |
| 3,731,453 | | 5/1973 | Porteous . |

(List continued on next page.)

FOREIGN PATENT DOCUMENTS

| 4444547 | 6/1996 | (DE) . |
| 0345659 | 12/1989 | (EP) . |
| 0412283 | 2/1991 | (EP) . |
| 0743250 | 11/1996 | (EP) . |
| 2693369 | 1/1994 | (FR) . |
| 2010681 | 7/1979 | (GB) . |
| WO8605172 | 9/1986 | (WO) . |

OTHER PUBLICATIONS

Neue Verpackung, No. 3, 1988, pp. 50–52.
Drugs Made in Germany, vol. 30, pp. 136–140 (1987).
Pharm. Ind. 46, Nr. 10 (1984), pp. 1045–1048.
Pharm. Ind. 46, No. 3 (1984), pp. 317–318.
Vetter Lyo–Ject Brochure (1984).

*Primary Examiner*—Richard K. Seidel
*Assistant Examiner*—Jeremy Thissell
(74) *Attorney, Agent, or Firm*—Dinsmore & Shohl LLP

(57) ABSTRACT

A syringe type ampoule having a) a barrel with a front end and a rear end defining an axis therebetween, the barrel having substantially constant cross-section between the front end and the rear end, at least the front end ending in an opening, b) a sealer attached to the front end and sealing the opening, c) at least one piston movably and sealingly arranged within the barrel and d) a sleeve extending along at least a part of the barrel, the sleeve having a front part and a rear part, the front part being connected to the sealer. The barrel has a front end terminating in an edge surrounding the opening, the edge having an outer circumference substantially equal to the barrel outer circumference. The invention relates to methods and means for manufacture of pre-filled such ampoules or other ampoules.

273 Claims, 5 Drawing Sheets

U.S. PATENT DOCUMENTS

| | | |
|---|---|---|
| 3,810,469 | 5/1974 | Hurschman . |
| 3,834,526 * | 9/1974 | Zine, Jr. .............................. 206/528 |
| 4,039,309 | 8/1977 | Albanese et al. . |
| 4,142,633 * | 3/1979 | Raghavachari et al. . |
| 4,235,235 | 11/1980 | Bekkering . |
| 4,553,962 | 11/1985 | Brunet . |
| 4,682,003 | 7/1987 | Minakawa et al. . |
| 4,729,208 * | 3/1988 | Galy et al. .............................. 53/432 |
| 4,774,772 | 10/1988 | Vetter et al. . |
| 4,865,090 * | 9/1989 | Burolla et al. ...................... 141/165 |
| 4,968,299 | 11/1990 | Ahlstrand et al. . |
| 5,139,490 | 8/1992 | Vetter et al. . |
| 5,185,985 | 2/1993 | Vetter et al. . |
| 5,360,410 | 11/1994 | Wacks . |
| 5,435,076 | 7/1995 | Hjertman et al. . |
| 5,498,243 * | 3/1996 | Vallelunga et al. . |
| 5,501,673 | 3/1996 | Hjertman et al. . |
| 5,573,042 | 11/1996 | De Haen . |
| 5,590,782 * | 1/1997 | Haber et al. ........................ 206/528 |
| 5,637,100 | 6/1997 | Sudo . |
| 5,700,246 * | 12/1997 | Stiehl et al. ........................ 604/198 |
| 5,716,338 | 2/1998 | Hjertman et al. . |
| 5,779,753 | 7/1998 | Vetter et al. . |
| 5,810,885 * | 9/1998 | Zinger ................................. 606/213 |
| 5,911,253 * | 6/1999 | Webb ................................. 141/243 |

\* cited by examiner

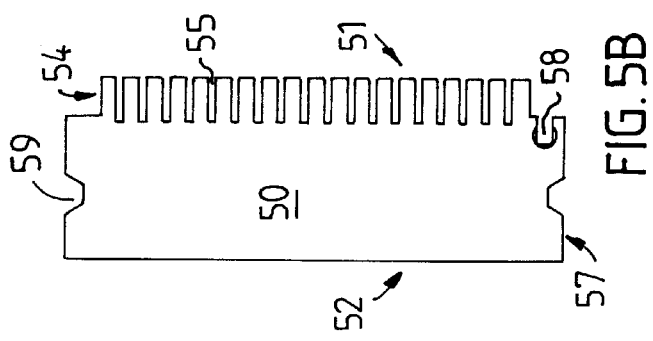
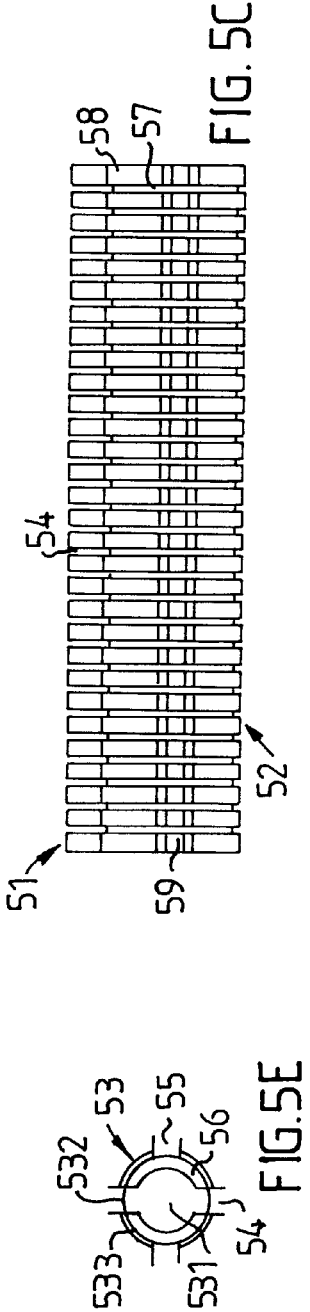
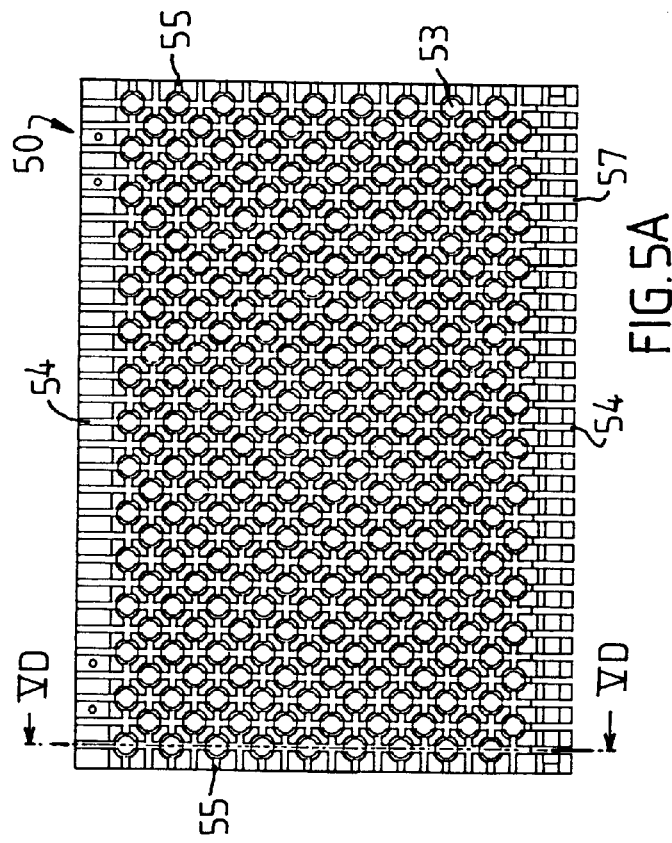
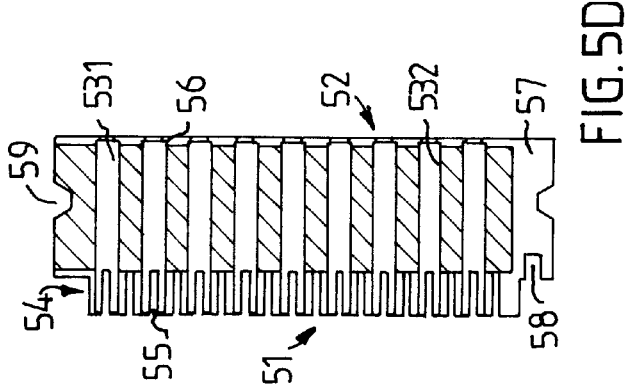

PREFILLED AMPOULES AND MANUFACTURE THEREOF

PRIORITY

This application claims benefit to U.S. Provisional application Serial No. 60/061,399 filed Oct. 6, 1997, and to prior foreign application in Sweden S.N. 9703425-0 filed Sep. 23, 1997.

TECHNICAL FIELD

The present invention relates to a syringe type ampoule having a) a barrel with a front end and a rear end defining an axis therebetween, the barrel having substantially constant cross-section between the front end and the rear end, at least the front end ending in an opening, b) a sealer attached to the front end and sealing the opening, c) at least one piston movably and sealingly arranged within the barrel and d) a sleeve extending along at least a part of the barrel, the sleeve having a front part and a rear part, the front part being connected to the sealer. The invention also relates to method and means for manufacture of prefilled ampoules.

BACKGROUND

Ampoules prefilled with various components are manufactured for diverse purposes. The present invention is mainly concerned with products of this kind for applications in which the demands are especially high. A representative example is prefilled ampoules for medicals or medical applications on which are placed severe demands quite generally for integrity, sealing, sterility, purity, amounts, rigidity etc. The ampoules can be plain breakable ampoules, sealed vials etc. More elaborate ampoule types further push the demands. Syringe type ampoules for example add considerations to piston friction and sealing and restrict front end sealing options. Dual or multi chamber type ampoules additionally require openable sealings between chambers and arrangements for mixing or reliable sequential delivery. Although the present invention have a more general utility it will mainly be described in terms of these demanding applications.

Each product quality and tolerance demand translates into corresponding manufacturing problems. Generally many components and process steps are required with intermediate controls. The components as such may be a contamination source as when glass, rubber or aluminum particles are released from ampoules, sealings and cappings respectively. Most steps have to be conducted in a pure or even sterile zone with the exception of some initial and final steps. Use of human operators in sterile environments is cumbersome and the fully mechanized alternative becomes complicated when increasing the number of steps and components involved. Bulk handling of components is simple but tend to increase problems with component damage, destruction and particle release. Individual manipulation on the other hand complicates machinery and reduces throughput. Use of cassettes or carriers for multiple components only represents a tradeoff between the extremes. When the ampoules are to contain a lyophilized compound there are further constraints on the equipment used as several steps, such as closure of the ampoules, has to be conducted within a closed freeze-drying chamber and should provide for e.g. vapor transfer and uniform heat exchange and should be compatible with the necessary temperature and pressure changes involved. Syringe type ampoules generally give limited access to the interior as the openings are mainly adapted for the pistons and needle attachments and temperature and pressure changes may displace pistons inserted. Multi-chamber ampoules further add to processing and may require turning and two-way access and the additional features, such as by-pass structures, complicate manipulation.

A typical dual-chamber syringe and a process for automated manufacture of prefilled such syringes is disclosed in Neue Verpackung, No.3, 1988, p. 50–52; Drugs Made in Germany, Vol. 30, Pag. 136–140 (1987); Pharm. Ind. 46, Nr. 10 (1984) p. 1045–1048 and Pharm. Ind. 46, Nr. 3 (1984) p. 317–318. The syringe type ampoule is a dual chamber device with a front bottle type opening for needle attachment, two pistons and an exterior type by-pass for mixing a lyophilized powder in the front chamber with a reconstitution liquid in the rear chamber. The process described includes the main steps of washing and siliconizing the syringe barrels, insertion of multiple barrels in carrier trays, sterilization, introduction of middle piston through barrel rear end, turning the trays upside down, introduction of the powder solution through the front opening, lyophilization to dry powder, closure of front opening while in the lyophilizing chamber, turning of trays, introduction of the reconstitution liquid through barrel rear end, insertion of rear piston, removal of products from trays and final control and packaging. This known process express most of the general problems outlined above. It is highly restricted to the specific product processed, e.g. by requiring a special closure system and by having the barrels resting on the exterior by-pass structure in the trays.

A general problem with prior art devices is the limited considerations to combined manufacturing and construction simplicity. The U.S. Pat. No. 5,435,076 discloses a dual chamber syringe construction with reduced demands for attachment and holding structures on the ampoule proper, still with features facilitating manufacture. In embodiments shown a central barrel is surrounded by a sleeve extending from a front opening to barrel rear end, thereby making superfluous any and all fastening structures on the barrel itself. At the opening the sleeve acts to secure a sealer in sealing position and eliminates the need for a separate capping. At the rear end a fingergrip, a plunger or a delivery mechanism can be attached to the sleeve part. In spite of barrel simplicity sealer and sleeve may, if desired, be joined into a single closure component allowing sealing in a simple axial movement, also in a lyophilizing chamber. Whenever present in the manufacturing process the sleeve also protects the central barrel and, e.g. in case of damage, confines or restricts barrel debris from spreading to other products or the plant itself. Yet there are room for improvements, especially adaptations for manufacture in highly automated processes.

Accordingly there remains a need for both ampoule constructions and ampoule filling processes and equipment better suited to meet high demands in the production of prefilled ampoules.

SUMMARY OF THE INVENTION

A main object of the present invention is to offer a system of ampoule constructions, manufacturing methods and manufacturing equipment better meeting the demands and avoiding the problems described. A more specific object is to offer a system in all its components simplified in relation to existing art. Another object is to offer a system easily adaptable to product variations. Still another object is to provide a system suitable for application in highly automated manufacture. Yet another object is to provide a system suitable for use with lyophilizing steps. A further object is to provide a system suitable for manufacture of syringe type ampoules and especially dual or multi chamber ampoules. Still another object is to provide a system allowing manufacture of improved reliability, less malfunction and more reproducible results.

These objects are reached with the characteristics set forth in the appended patent claims.

The invention may be used with the already improved syringe type device described, having a sleeve around a central barrel. According to the invention such a device can be still more simplified by using a barrel of substantially the same diameter at its front opening as its overall diameter, allowing use of e.g. a plain cylinder. This design further facilitates filling operations through the front opening but above all allows a piston to be inserted through the front opening and not only through the rear opening, which may be used to reduce necessary manufacturing steps and facilitate equipment design by allowing more steps to be conducted form the same side. The design also makes it easier to use a sealer or stopper for the front opening extending out to and beyond the barrel diameter. In the product this property allows the sealer to better center and buffer the external sleeve and in manufacture the same property makes it possible to grip and hold the sealer in an equipment cavity adapted to the barrel diameter, which in turn may be used to eliminate use of the sleeve for sealer manipulation, making sleeve design more free, e.g. in respect of barrel to sleeve distance, and enabling removal of the sleeve from at least the sterile manufacturing zone and enabling independent inspection of the barrel ampoule semi-manufacture. Use of a barrel with a front opening edge being rounded with the edge material kept within the nominal barrel inner and outer diameters further amplifies these advantages. The property also gives general advantages in bulk or individual handling of the barrels as such, e.g. higher precision and strongly reduced risk for damage and particle release. Sealers and stoppers can more easily and without tumbling risks be attached to the opening with mechanized means, also in the absence of the sleeve as sealer manipulator, and the stoppers as such can be made less elaborate and with less cavity forming parts within the barrel. The invention also provides an ampoule carrier giving substantial general advantages in manufacture of prefilled ampoules. The carrier can be used in most manufacturing steps, reducing bulk treatment and corresponding damage risks for the ampoules. The carrier provides one or more channels for individual ampoules. Channels formed as a cavities in a carrier body and essentially surrounding the ampoule give a protection and contamination confinement similar to the known sleeve. The cavity has been found to assist in a uniform heat conduction and radiation shielding of special importance in lyophilizing processes. If desired the cavity can be made to radially support an ampoule over substantial length and the structure can be made, e.g. by spacers or otherwise, to accommodate ampoules of different lengths or widths, thereby providing a valuable versatility. Although not restricted to any particular ampoule form the structure cooperates beneficially with ampoules of the general cylindrical form described. A channel made longer than the ampoule can be used to hold a sealer in a floating, and yet protected, position above but concentric with the ampoule opening for later individually centered and guided axial movement into a closed position, an option of particular value in lyophilization, for allowing first vapor passage past the sealer and later in-situ closure of the powder chamber. When used with a cylindrical barrel type ampoule and slightly oversized sealer as described, these advantages can be obtained with maintained possibilities for ampoule introduction in the channel from the sealer seat side of the carrier, without additional guiding structures. Upper and lower locking surfaces protruding into the channel can be used to restrict ampoule axial movements. A surface separation of at least ampoule height allows the ampoule to reside between the surfaces. A first advantage with this feature is that ampoule ends are used for axial fixation making superfluous any intermediate structures, such as flanges, recesses, bottle neck openings, by-pass structures etc., and accordingly makes the carrier compatible with the most pure ampoule designs described. A further advantage is that all forces applied to the ampoule during manufacture, such as in insertion, filling, piston introduction, sealing and removal, are absorbed in the beneficial axial direction, strongly reducing the risks for ampoule damage and plant contamination. Still, releasable locks may make both channel sides accessible for operational steps, both the direct manufacturing steps but also indirect steps, such as probing and ampoule weighing, providing substantial flexibility in use, especially in combination with turnable carrier arrangements, of value in plants for multiple ampoule types or multiple chamber type ampoules. Movable locking surfaces may be complemented with stop surfaces fixed relative each channel to further reduce the risks for inadvertent compression and excessive forces, of value for example when exact tolerances in size or support cannot be guaranteed.

Further objects and advantages with the invention will be evident form the detailed description hereinbelow.

DETAILED DESCRIPTION

As indicated in the introduction the injector described herein may be used for a variety of purposes within and beyond the medical area and for any type of preparations, such as chemicals, compositions or mixtures, in any container and used for any purpose. For reasons outlined the system has certain special values in connection with medical delivery devices where also the design constraints are more severe than in most other applications.

The principles of the present invention may be used for ampoule devices or systems in broad terms. It is possible to use the principles of the invention for manufacture of the ampoules as such, i.e. empty ampoules, e.g. for later filling or for use as mixing or preparation chambers, but it is preferred to use the invention in connection with pre-filled ampoules and manufacturing methods therefore, i.e. including filling steps. The nature of the material prefilled or after-filled into the ampoules is not critical and shall be understood to include gases, liquids and solids. The material may be a powder, e.g. a powder, a cake or a tablet. The material may be a fluid such as a liquid, including materials behaving as liquids such as emulsions or suspensions. The material may undergo transitions as when a solid is dissolved or a solution is dried, which may take place in the manufacture or as a final preparation or mixing step immediately before use. The nature of medical contents shall also be understood to include medical in broad tenns and to embrace for example natural components and body fluids prefilled or drawn into the container although most commonly the medical is factory prepared. The invention may assist in solving special problems in connection with sensitive compounds susceptible to degradation or denaturation under mechanical stress such as high shear forces. Compounds of high molecular weight may be of this type, high molecular weight hormones for example growth hormones or prostaglandins. The invention may also assist in solving special problems in connection with medical requiring lyophilizing step in production or a preparation step immediately prior to the infusion, typically a mixing of two or more components, which all may be fluid or may include a solid as when dissolving a lyophilized powder in a solvent, such as hormones or prostaglandins.

The Ampoule

The "ampoule" shall be understood in broad sense and can generally be said to include a container part and at least one opening for access to the container interior. Unless otherwise indicated the opening shall be regarded as defining an ampoule axis, being perpendicular to and centered within the opening surface or, in flow sense, being parallel with and centered within a hypothetical flow through the complete opening. A direction along the axis through the opening from the container interior and to the container interior shall be regarded as forward direction and rearward direction respectively. When two or more openings are present the said at least one opening, or reference opening, shall be an opening to be sealed in the process and if the ampoule comprises two or more such openings to be sealed, the reference opening shall be an opening in end use intended for passage of the prefilled material from the ampoule interior out through the opening. A distance between ampoule frontmost and rearmost ends shall be considered ampoule height or length. Positional and directional statements will be given in relation hereto unless otherwise stated.

The container has at least one opening through which the container content can pass during use of the ampoule, either from the container interior to the surrounding for e.g. administration of the medical to the patient or to the container in case of aspiration of body fluids or during preparation steps such as filling, mixing or dissolution in the container. Several openings may be present, notably front and rear openings in a tube type container. The same opening or openings may be utilized for communication both at manufacture and administration or different openings can be used, e.g. filling through and sealing one opening and delivering through another opening which may be closed with a releasable or rupturable sealing.

The opening physical structure may need adaptation to its use purpose. A syringe type ampoule plunger end may need an opening allowing insertion of a piston and perhaps end structures for connection to a fingergrip, a plunger or a delivery mechanism. The other end, like the opening of a vial, may need arrangements for a closure or a sealing. For this purpose some kind of physical attachment for the closure means can be arranged, e.g. protruding or recessed structures for cooperation with complementary shaped closure parts. These structures may be located on the opening interior, exterior or both. Although threads or bayonet type structures are conceivable it is preferred to use structures allowing engagement with a simple axial relative displacement between container and closure, without requirement for substantial angular motions. Such structures may include circumferential flanges, grooves, undercut etc., continuous or intermittent, around the opening, including the common bottle-type with orifice flange, neck and shoulder parts. Several such structures may be used, e.g. axially displaced for example in order to assist positioning of closure parts in an open position, allowing gas exchange, and a closed position, although other arrangements to be explained are preferably used for this purpose. For similar reasons to be explained there are advantages in using a plain tube shape opening, without the abovesaid structures, which can be closed with an inserted simple plug or stopper type sealing or any kind or closure, such as a flat abutting type sealer, in combination with the abovementioned sleeve fixture. It is clear that the ampoule in general terms is compatible with various opening structures as well as various closure structures, including known common types such as resilient sealers with or without cappings for permanent seal or penetrable or rupturable arrangements.

The container part may take a variety of forms such as any kind of tube, vessel, flexible bag, vial, capsule, cartridge, capsule, syringe body etc. There are some advantages in using containers that are rigid, at least at its opening, but preferably generally rigid, such as vials, rigid tubes or syringe bodies. There are also some advantages in using roughly symmetrical container parts, being at least partly symmetrical with constant cross-section around an symmetry axis, such as a bottle body or cylinder type container, and preferably the opening axis and the container axis are substantially parallel and most preferably substantially coaxial. Still more preferred is to use the same cross-section profile for both container and opening, giving an elongated ampoule of essentially uniform shape from front end to rear end, as exemplified by a cylinder, with or without closed rear end as for a vial. Common container materials such as plastic or preferably glass can with preference be used. The container may be an integral or composite structure, such as including an outer casing or any other multipart construction for closures, fixtures, protection etc., and unless otherwise stated "container" shall be understood to include any auxiliary part present.

The ampoule may be a simple bottle, vial or bag but the invention has special value in connection with more advanced ampoule types and preferably the ampoule type is more elaborate and is commonly in the form of a cartridge, being the ampoule part of a syringe type of delivery system, which may be still more elaborate in the case of multichamber cartridges. A cartridge for the present purposes may generally be said to include a barrel having a front part and a rear part defining a general cartridge axis, an outlet for the preparation arranged at the front part and at least one movable wall arranged at the rear part, a displacement of which wall causes the preparation to be moved towards or expelled through the outlet. Barrel shape and movable wall have to be mutually adapted. The barrel may have a substantially constant internal cross-section, with a similarly constant barrel axis, between front and rear parts giving a generally tube-shaped barrel, and most preferably the cross-section is of the common circular type giving a substantially cylindrical barrel. The movable wall is then preferably a substantially shape-permanent, although possibly elastic, body sealingly adapted to the internal barrel surface and preferably of the piston type.

Dual or multi chamber cartridge types are known e.g. for preparations demanding a mixing of two or more components or precursors before administration. The components are kept separated by one or more intermediate walls of different known designs, which walls divide the barrel into several chambers, sometimes placed parallel along cartridge axis but most commonly in stacked relationship along the axis. Unification of the components may take place by breaking, penetrating or opening a valve construction in the intermediate walls, for example by introducing a pin or needle through the cartridge front, through or at the rear movable wall or by means at the cartridge exterior (compare e.g. WO 93/02720). In another known design the intermediate wall or walls are of the plunger type and flow communication between the chambers is accomplished by moving the plunger to a by-pass section where the interior wall has one or several enlarged sections or repeated circumferential grooves and lands in a manner allowing by-flow of rear chamber content into front chamber at displacement of the rear movable wall (compare e.g. U.S. Pat. No. 4,968,299 or WO 93/20868 and WO 95/11051). The latter type of by-pass is preferred by allowing ampoule designs of substantially constant cross-section. The chambers may contain gas, liquid or solids. Generally at least one liquid is present. Most commonly in pharmaceutical applications only two chambers are present and typically contains one liquid and one solid, the latter being dissolved and reconstituted during the mixing operation.

As common in the art the ampoules, cartridges or syringes described may be adapted for connection to a delivery conduit. The delivery conduit may be an infusion channel or any conducting means such as a tube or catheter, a needle or cannula or a needle-less system based on liquid jet or a particle gun with gas propellant. The conduit shall be connectable to the container interior, preferably via one ampoule opening, such as by connection to an openable, rupturable or penetrable sealing.

Preferred Syringe Type Ampoule

Although the system of the invention incorporates manufacturing methods and means useful for all of the ampoule types described the system also includes an ampoule type of special value in the system. As indicated in the introduction the preferred syringe type has a) a barrel with a front end and a rear end defining an axis therebetween, the barrel having substantially constant cross-section between the front end and the rear end, at least the front end ending in an opening, b) a sealer attached to the front end and sealing the opening, c) at least one piston movably and sealingly arranged within the barrel and d) a sleeve extending along at least a part of the barrel, the sleeve having a front part and a rear part, the front part being connected to the sealer.

In such a device the requirement for substantially constant cross-section shall not exclude minor deviations as for example attachment structures at the front and rear end or an intermediate by-pass structure, although it is preferred to make all such deviations as small as possible, e.g. expressed as maximum to minimum diameter less than 2 mm, preferably less than 1 mm and preferably less than 0.5 mm and most preferably substantially nil. When used herein "diameter" shall not be understood as a limitation to circular cross-section profiles but shall generally mean diametrical points on the outer circumference for non-circular profiles.

Yet, it is preferred that the barrel cross-section is substantially circular making the barrel subtantially cylindrical. The barrel can with advantage be of dual or multi chamber type, incorporating at least one by-pass arrangement. Of the by-pass arrangements earlier exemplified it is preferred to utilize such arrangements that do not substantially affect the outer diameter of the barrel, such as internal arrangements or distributed lands and grooves design exemplified. Similarly it is preferred that barrel cross-section area is substantially constant between front and rear ends since any deviation either makes the barrel bulkier than necessary or weaker than necessary. Accordingly it is preferred that attachment structures, channels, by-pass cut-outs etc. are avoided or kept to a minimum, e.g. that cross-section area variations anywhere along the barrel axial length are kept less than 20%, preferably less than 10% and most preferably less than 5%.

It is also preferred that the opening has substantially the same cross-section profile as the barrel, making the opening substantially a continuation, or ending, of the barrel and suitably the opening edge roughly corresponds to a cross-section of the barrel perpendicular to the barrel axis. It is also preferred that the opening part is included in the abovesaid constant cross-section area conditions stated for the barrel as a whole. This overall edge shape does not exclude that the form of the mere edge termination, e.g. when seen in an axial cross-section, is trimmed to suitable shape for its purpose. It is for example common to make edges generally of smooth form in order to avoid fracture risks, release of particles, cutting wounds, stopper jamming etc. Such a rounded forms is preferred, for either the inner or the outer part of the edge cross-section and preferably both, and can be accomplished by grinding but is preferably made by heating for meltable materials. Melting may, however, make the melted material contract into a quasi-drop form when seen in said axial cross-section, with a largest drop diameter exceeding material thickness before heating, i.e. a partial drop larger than a semi-circle. Applied to the present barrel the edge may protrude into the barrel interior and/or out from the barrel exterior. It is preferred, e.g. for maintaining a uniform barrel exterior and facilitate handling, to make the edge form so that substantially all edge material is kept within the barrel external diameter. Similarly it is preferred to make the edge form so that substantially all edge material is kept outside the barrel internal diameter, which facilitates access through the opening during manufacture, e.g. at filling and piston or sealer insertion. It also facilitate sealer design by requiring less pronounced wedge angle and length for any part entering into the opening, which in turn facilitates engagement and reduces dead and shielded spaces within the sealed chamber. Expressed in drop form terms it is preferred that the edge curvature corresponds to about a semi-circle or slightly less. A preferred manufacturing method for a smooth and yet narrow edge is to heat a blank barrel raw material around the desired edge profile and separate the parts by axial pulling while the heated edges are still hot and possibly under maintained heating. The heating can take place by conventional means such as a flame but is preferably made by laser, notably a carbon dioxide laser for glass, for most narrow heating zone and best overall control, or a combination of the heating methods. This heating and pulling separation method is known as such for other applications and dis5 closed for example in WHO 86/05172, U.S. Pat. No. 4,682,003 and DE 4444547. Although the opening structure can be provided with other structures, such as cut-outs or channels on the interior surface of the barrel close to the opening to allow gas exchange with the surroundings, e.g. at lyophilization, also with a partially inserted sealer, it is preferred to use other methods and means for this and make the barrel part close to the opening substantially uniform, e.g. for simplicity and best sealing properties. The above considerations preferably apply for an opening to be at least temporarily closed or sealed, notably the front opening of the syringe type ampoule, i.e. the side for preparation ejection but can with advantage also be used for the rear opening normally used for affecting the rear piston.

The sealer used to seal the front opening can be of any general nature described. It may have an already provided opening for fluid communication with the barrel interior and/or an already attached conduit or attachment means therefore. It is, however preferred to use sealers making a complete seal for later opening or attachment of a conduit, preferably any of the sealers suited for penetration. It is further preferred to use sealers that can be brought from a non-sealing position into sealing contact with the opening by use of a simple axial displacement. The sealer can be of the kind providing sealing by axial pressure against the opening edge, e.g. having a flat or flange portion corresponding to the edge, but it is preferred to use a stopper type sealer having a part penetrating into the opening and providing sealing by radial contact or pressure against the barrel interior, possibly and preferably in combination with a flange portion for axial contact with the edge. The part penetrating into the barrel can be generally cylindrical and may in a conventional manner have a central cavity, cut-out or recess to increase flexibility or limiting the necessary penetration length for a needle or other type of sharp. With preference the penetrating stopper part can have a wedge shape for assisting in proper guidance of the stopper lower rim radially towards the axis when inserted in the opening. The wedge-shaped portion can with preference be restricted to the lowermost part of the stopper penetrating part and the angle between axis and stopper lower surface is preferably made as large as possible, to avoid dead spaces, with regard to necessary guidance. Independent of sealer type selection, e.g. flat, flange and/or stopper type, it is preferred that at least a part, hereinafter a "flange" part, of the sealer has an extension in the radial direction, i.e. perpendicular to its axis when in place, larger than the barrel outside diameter. It is preferred that it is at least larger than the barrel diameter at the opening, which among others makes it radially accessible at the opening and beneficially cooperates with the sleeve at least at the opening. It is preferred that the sealer flange part is also larger than the largest diameter of the barrel, when this is not entirely uniform as exemplified above, making a flange diameter the largest diameter of the barrel/sealer unit, which amplifies the abovesaid advantages. Such an extension also allows the sealer to be frictionally or otherwise held, without contact with the barrel, in a channel of the same diameter as the barrel outside diameter, which facilitate automatic pushing of the sealer from a rest position in such a channel above the barrel into a sealing position in contact with the barrel opening. The channel of such a diameter also allows the barrel to move, or be inserted, past the rest position for the sealer. If the channel diameter is significantly larger than the barrel largest diameter it is preferred that the sealer flange is larger than the channel diameter. The degree of extension "larger" than the barrel diameter at the opening, its largest diameter or the channel respectively should be adapted for the stated purposes and may be dependent of the strength of the grip desired and the resilience or mate rial of the sealer etc. For example, in order to retain the sealer in the channel the diameter should in functional terms be adapted to provide sufficient friction to hold it in the method steps but not prevent is axial movement in the sealing step. The degree of extension may typically be at least 0.05 mm, preferably at least 0.1 and most preferably 0.2 mm larger than the diameter referred to. It can also be kept smaller than 10 mm, preferably smaller than 5 mm and most preferably smaller than 2 mm compared to the diameter referred to. It is sufficient that the flange has the stated extension at least somewhere along its periphery, e.g. at at least two diametrically opposed positions, better at at least three or more points, preferably symmetrically distributed around the periphery for best centering, and most preferably along substantially all of its periphery. Although such an oversized flange portion can be compressible enough to be inserted into the opening, it is preferred that the flange is designed to be positioned, when in its sealing position, outside the barrel and most preferably at a flat portion intended for axial contact with the opening edge. The sealer parts still more distant from the opening edge is not very critical. This axially distant end should, however, preferably be consistent with the purpose of cooperating with the sleeve to prevent axial displacements of the sealer away from the opening when the sleeve is in a locking position an preferably also be consistent with the purpose of allowing the sleeve to be axially moved in a rearward direction into said locking position when the sealer is in place. For these purposes the sealer preferably has a contact surface with at least a surface component normal to the axis against which a sleeve part can be abutted, e.g. a contact surface in the form of a flat rim against which a sleeve flange can be placed. Otherwise the sealer distal end can have any conventional form, e.g. a central part exposed for penetration, preferably in the form of a concave bowl to limit necessary penetration length. The sealer described is preferably made of a resilient material such as common rubber or elastomeric materials. Although possible if desired, in general the sealer need not be supplemented with a common capping to retain the resilient sealer, as the sleeve to be described preferably acts to fill this function.

The ampoule contains at least one piston axially movable within the barrel enabling a pump action relative the content, for example aspiration of material into the barrel and/or ejection of barrel content from the barrel, the latter in particular for prefilled syringes. In case of dual chamber devices and additional piston may be present, dividing the primary chamber between the rear piston and barrel front opening into a front and a rear chamber. In this case a by-pass may be present as described, either arranged at an intermediate position along the barrel to allow overflow from the rear chamber to the front chamber e.g. for mixing or dissolution or arranged close to the opening to allow first ejection of the front chamber content and then ejection of the rear chamber content through the by-pass past the intermediate piston. Three or more chamber may be devised by additional such structures. The piston can be of the conventional type being of resilient materials similar to those of the sealer and having a generally cylindrical shape.

The sleeve part shall be understood in a broad sense as any structure bridging the front and rear ends of the barrel. A main object of the sleeve is to retain the sealer against forward displacement relative the barrel for which purpose the sleeve should at one hand grip the sealer and on another hand be attached to the barrel in a manner preventing at least forward movements relative the barrel. Preferably the attachment to the barrel is made at the rear part of the barrel, which for example can be made laterally by an adhesive or at a special fixings structure such as a flange or a recess in the barrel, but it is preferred that the sleeve attach to the barrel by utilizing the barrel rear edge as a stop surface for sleeve forward movement, which principle allows use of a pure tube type barrel without any fastening structures. The attachment can be accomplished for example by a structure integral with or connected to the sleeve, that extends radially inwards from the sleeve main part for contact with the rear edge, e.g. a rear flange on the sleeve or a rear plate or fingergrip for a plunger to which the sleeve rear part is attached. Similarly, at the sleeve front end, the sealer can be gripped with lateral means but is preferably gripped in the axial direction by contact between a front surface of the sealer, as earlier described and a rearwardly directed surface of the sleeve, such as the rear surface of a sleeve flange extending radially inward from the sleeve main axial part. It is clear that in these preferred arrangements forces between sleeve and barrel are entirely axial in the barrel and sleeve main part. The sleeve main part, i.e. the part outside the barrel exterior extending between the front and rear ends, can be any spacer structure, such as a single rod or arm, two or more such arms distributed around the barrel circumference in a cage type structure or one or several tube parts. It is preferred, however, e.g. for protection reasons, that the sleeve extends substantially all around the barrel essentially enclosing the barrel, e.g. having a generally tube form. The sleeve can be a single internal structure but is preferably made of at least two parts for assembly reasons, e.g. with a separate front or rear part or two flanged tube parts for cooperation with barrel front and rear ends which parts are joined at an intermediate position. Auxiliary structures with preference can be arranged on the sleeve, rather than on the barrel, such as fastening structures, guiding structures, plunger and fingergrip structures, dosing mechanisms and needle attachment structures, e.g. to adapt the combined barrel/sleeve cartridge type unit for manual or mechanized and automated actuation and operation in a delivery device. In the radial direction the sleeve may make contact with the barrel but it is generally preferred that a distance is kept between these parts for tolerance and safety reasons. The actual distance depends on the barrel form, e.g. the presence of an external by-pass, but for the preferred barrel of substantially uniform cross-section over length the distance with preference can be kept small, such as less than 2 mm, preferably less than 1 mm and most preferably less than 0.5 mm. A sealer slightly oversized in the radial direction, as earlier described, here may contribute with the additional advantage of centering, guiding and buffering the sleeve relative the barrel.

The syringe type ampoule construction described, besides allowing extremely simple and pure barrel forms, has a useful manufacturing advantage in its wide front opening. This feature can for example be utilized to introduce a piston through the front opening, rather than through barrel rear end, which possibility in turn can be exploited to make several process step from the same barrel side, e.g. piston insertion, filling and sealing, perhaps repeated in multichamber ampoules, for example to facilitate machinery design, avoid turning steps and reserve the other barrel end for fixture, probing or other filling operations. In combination with the additional features explained other manufacturing advantages are reached as has already been indicated.

The Ampoule Carrier

According to the invention an ampoule carrier is provided for the purpose of facilitating and improving the manufacture and quality of prefilled ampoules. The carrier can be used for any of the ampoule types described although advantages are obtained in using ampoules with the preferred features stated. Generally the carrier can be said to comprise a) one or several seats for an ampoule, the seat providing b) a channel for axial insertion but radial retention of the ampoule.

As used herein "carrier" shall be understood to mean a device suited for carrying at least one and preferably several ampoules and suited to be handled as a unit in a manufacturing plant. The carrier can be monolithic but is preferably an aggregate of details handled as a unit. The carrier may comprise auxiliary features, i.e. features relating to the carrier as such, e.g. facilitating its handling in the process, such as details suited for mechanical gripping, turning and transportation as well as means facilitating assembly, disassembly and cleaning. When applicable the carrier "upper" and "lower" sides shall be regarded the side at the front end and rear end respectively of the ampoule when inserted in the carrier.

The carrier shall include at least one "seat" for each ampoule to be carried, i.e. one or preferably several seats, and the seat shall be understood to include any detail on the carrier adapted for the individual ampoules, such as individual retention and manipulation means. Preferably each seat is adapted to receive one ampoule only.

The seat comprises at least a "channel" for the ampoule, by which shall be understood any feature adapted for allowing axial insertion or movement but radial retention of the ampoule. The channel may for example include one or several plates or other spacing structures providing radial support of the ampoule at discrete locations along its axis. Preferably, however, channel comprises a "cavity" in the sense of a chamber surrounding the ampoule over substantial length and most preferably over its entire length. The cavity can for example be formed as a "bore" in a monolithic body part of the carrier.

The seat may also comprise one or more "locks", meaning any structure for retaining the ampoule in the axial direction. A lock may grip the ampoule at any part, e.g. intermediate part, and prevent movement in both the axial directions. Preferably, however, a lock acts as a stop surface at the ampoule end, thereby preventing ampoule movement in one direction. Preferably two locks are arranged, one in each end of the channel, preferably with a distance of at least ampoule height but possibly a larger distance. It is further preferred that at least one, and preferably all, locks are releasably arranged to allow access and ampoule insertion and removal.

The seat may comprise further auxiliary details, such as guiding structures for tools, a position for the sealer, venting channels for gases, etc.

Constructively the carrier can preferably be arranged as an intermediate body part, embracing most of ampoule height and channel length, an upper head part with e.g. an upper lock and auxiliary details and a lower foot part with e.g. a lower lock and possible auxiliary details. The height of the body part may be adapted to the length of the ampoules treated. The body part can be a frame type of structure, e.g. two or more plates with holes, forming the channels, the plates being separated with spacers and possibly walls to enclose the frame. Such an open structure may be lightweight and easily adaptable to varying ampoule lengths. It is preferred, however, that the body part is formed as a unitary structure, preferably monolithic, in which the channels are formed as longitudinal cavities, e.g. bores, at least partially open at the upper and lower ends of the carrier body part. Such a unitary structure facilitates the arrangement of a cavity enclosing the ampoule, which is advantageous for reasons set out in the introduction and preferably the cavity has at least the same height as ampoule length.

Generally it is preferred that the channel length at least corresponds to ampoule length, e.g. not to expose any end thereof when handling the carrier, but it is preferred that the channel is longer, in particular at the upper end for the purpose of at least holding, but preferably also enclosing, a sealer in a non-sealing position relative the ampoule opening, e.g. as a preparation for pressing the sealer into a sealing position and preferably also for the purpose of allowing lyophilization. As known per se, the sealer position may be in a partially inserted position relative the opening, as when vapor channels are arranged in the sealer or the ampoule, but preferably the sealer position is farther forward and only resting on the opening edge but most preferably the sealer position is still farther forward in a floating position above and without contact with ampoule opening, e.g. to allow good gas communication even at simple ampoule and sealer structures, and which is easily accomplished by using the channel for holding the sealer. Channel width at the support points for the ampoules is preferably about the same as the ampoule largest width, allowing for a certain additional play or tolerance. Similarly the channel cross-section profile is preferably about congruent with ampoule cross-section profile, possibly with some deviation, e.g. to allow passage of a protruding structure such as an external by-pass when present. It is preferred that the channel has substantially constant cross-section at least along the ampoule height and preferably the cross-section profile or circumference forms a closed loop. When the channel is longer than ampoule length it is preferred that also the additional channel length has substantially the same width and profile, allowing the ampoule to be axially displaced therein. Accordingly, although a sealer can be held in that channel part by protrusions into the channel it is preferred that the sealer is held by friction against the channel walls, for which purpose the sealer preferably can be oversized as described.

A lock for restriction of ampoule axial movement and acting on the ampoule end as described may provide a surface extending into the channel part occupied by the ampoule to such an extent that it is able to support an end part of the ampoule. The lock should also be attached to the carrier, e.g. at its upper or lower part or at the channel upper or lower end. The attachment can be permanent, such as when the lock is an integral part of the carrier or otherwise permanently attached thereto. A permanent lock can for example be used at one channel end when the ampoule is inserted and removed through the other end and this may be sufficient if all manufacturing steps can be conducted form one end and there is no need to turn the carrier upside down. Releasable locks can be used as permanent locks but give higher flexibility and can be used to lock the channel side from which an ampoule is entered and in case of two such locks are utilized both channel sides are accessible for manufacture steps or insertion and/or removal of ampoules. A releasable lock may be attached by any type of fixture, e.g. for complete removal or hinged release. Although releasable locks can be designed as a plurality of individually releasable structures, one for each ampoule channel, it is preferred that a single locking structure is used for locking several and preferably all the channels, e.g. a plate or a grid, the attachment of which to the carrier locks all the several channels. The exact nature of the resting surface can be varied. The lock surface may completely close the channel end to which it is attached, e.g. as by a plate or multiple stopper type structure, but it is preferred that the surface only covers the channel opening partially, thereby allowing access to the ampoule also with the lock in place. The lock can with preference partially cover the channel so that a tool can be inserted through the uncovered part in order to lift or push the ampoule axially away from the lock. In case of a bottle type of ampoule this can be achieved through almost any uncovered part but in case of a tube type of ampoule, e.g. a cylindrical barrel, this may require that at least a part of the edge is exposed, e.g. by use of a locking surface in the form of a diametrical bar over the channel end or a flange covering only a part of the barrel edge. In case the ampoule has an opening at the lock, as the front or rear opening of a barrel, it is equally preferred that the opening is accessible and preferably completely accessible, e.g. for piston or sealer insertion, which again may require that the lock only covers the edge or a part thereof.

It is preferred to equip the seats with at least one lock, say at the lower channel end, on which the ampoule rests when performing operations at the other channel end, say the upper end, e.g. operations such as piston insertion, filling, floating sealer insertion, lyophilization and final sealing. It may be desirable to equip also the upper end with locks, e.g. to permit operations on or at the lower end after having concluded the operations at the upper end and which operations at the lower end may require retention of the ampoule or turning the carrier upside down, e.g. operations like rear compartment filling and rear piston insertion.

Separate tools, other than the lock structures, can be utilized in any such operation exemplified, for example conventional press pins can be used to insert or move pistons, sealers or the ampoules themselves and charging nozzles can be used to perform filling operations. Such individual tool parts for each channel can with preference be arranged on a common support, with or without pressure equalizing means, for common manipulation. It is preferred, however, to employ the locks also for at least one manufacturing step. To this end the lock structure with preference may be combined with other auxiliary details at this channel end. As has been described it may be of interest to arrange for retention of a sealer at an ampoule opening, which subsequently is pushed into engagement with the opening. Here the lock with preference can be arranged to bear on the sealer top when pushed into engagement. It is further preferred to use the same structure both for pressing the sealer into engagement and for subsequently acting as lock for the channel. The pushing movement with the lock structure can with preference be guided, by for example recesses into the carrier body, and these recesses can also act to limit the rearward movement of the structure to that required for sealer engagement and no more so as not to hurt the ampoules proper but the recesses may additionally be used as vapor channels in a lyophilization or sterilization step. Similar guiding structures may be arranged at the lower end if alternatively the sealer engagement is made by pushing the ampoules from below towards a sealer by use of the lower lock, whereunder the sealer may be kept stationary by use of an upper lock or a plate. For the combined purposes the lock may have the same tool design mentioned but with preference can be given a form suitable for both purposes. Lock structures in the form of long "knifes" or stiff bands, placed with their sharp or narrow edge towards the channel end, and accordingly with their broad surface axially, and spanning diametrically over several channels in a row, has been found suitable for the combined purpose, among others by retaining partial access to the channels, ease of axial guiding in longitudinal recesses along the carrier surfaces, which recesses preferably are present at each channel, option of combining with venting passages, simple release and fixture, possibility of burying within carrier body etc. Although recesses for guidance of such lock structures can fulfill several purposes, such as both movement limitation and gas passages, it is possible to used different recesses for such purposes. e.g. elongated recesses for the lock structures and other recesses for gas passage, such as holes or elongated recesses running parallel or preferably at an angle to the firstmentioned recesses such as perpendicular thereto.

Use Method

The method of using the carriers should be clear from the constructional description given, the rational for each feature and the operational steps exemplified. The versatility and flexibility provided by the characteristics stated enables numerous manufacturing schemes to be conducted, both conventional procedures and improvements according to the invention. Generally a preferred use method can be said to include the steps of inserting an ampoule in a channel, filling material into the ampoule, sealing the ampoule opening with a sealer and removing the ampoule from the channel.

An advantage of the invention is the possibility to conduct numerous step from each side of the carrier. The possibility of supporting the ampoules at their ends for example makes it possible to insert the ampoules from one carrier end, preferably the upper and upright end, and perform filling through the same end, preferably without any turning of the ampoules or carrier. It is also possible to insert a sealer from the same end, optionally performing a lyophilization step in the same position, and to perform the actual sealing step by pressing from the same channel end and, if applicable, remove the ampoule by reversing the ampoule inserting step. These steps may conclude the filling operations for a single chamber type ampoule, e.g. a bottle, vial or single chamber syringe. Yet the other carrier side and channel ends are available for supplementary or additional steps. For example, when manufacturing pre-filled dual or multi chamber devices, without an initial chamber separating wall, an intermediate piston may first be inserted to create two chambers. This can be done from the front or upper end, as just described for a single chamber device, if the ampoule has the preferred construction earlier described or from the other carrier side in case of any barrel design. After concluding the above described filling operations for the first chamber, the front sealed ampoules can be turned upside down, preferably with locks at that end in place, and a similar filling operation be conducted from the other end, possibly concluded with the insertion of a rear piston in case of a syringe type ampoule. This filling procedure from different ends is of special value when the components cannot be allowed to come into contact, even in trace amounts, during the manufacture or when the second component cannot be allowed to be present under a first set of steps, such as a pressure sensitive liquid during a lyophilization or sterilization step. Without such restrictions the invention allows filling of several chambers from the same end, equally well from either end, a property also of value in manufacture of pre-filled multi chamber ampoules.

It is advantageous to use the carrier in procedures involving a gas exchange step between the ampoule interior and the surroundings, among others because it is possible both to protect the ampoules and to arrange gas channels. It is also suitable to use the invention connection with method steps involving heat transfer, among others because of the suitable heat conduction and heat equalizing properties of the carrier. It is further suitable to use the invention in connection with procedures involving pressure changes, among others because of the abovesaid gas channels serve to allow the necessary pressure adaptations and because the filling flexibility makes it possible to delay introduction of pressure sensitive material, e.g. material moving, expanding or condensing under pressure differences or deteriorating under certain pressure or temperature conditions. Typical manufacturing steps involving these problems in connection with medicals are sterilization and lyophilization.

A preferred use is when passing a gas through tube type ampoules, such as barrels, from one end to the other which is facilitated by the carrier options of having at least partially exposed ampoule ends. With preference the carrier channels are substantially unobstructed, e.g. without sealers, in such a step. The gas may passed through the ampoules for any purpose such as washing, drying etc. but a preferred application is in gas sterilization of the ampoules. The gas may act chemically but it is preferred to use a hot gas, utilizing the carrier heat conducting advantages as described, e.g. as in a sterilizing oven with hot gas circulation.

Another advantage of the invention is the option of resting a sealer in a floating position above an ampoule opening, among others because it facilitates guided and protected engagement of the sealer by for example a simple axial movement between sealer and ampoule and because it is possible to conduct process steps between sealer introduction in the rest position and its engagement in the ampoule opening. Hence it is advantageous to use the invention in connection with procedures involving any such operation or generally a sealing step from a sealer rest position. A typical example is a lyophilization step in which the sealer can be inserted in the rest position and freeze-drying be conducted followed by sealer engagement, which last step easily can be performed within the lyophilization chamber due to the simple axial sealing movement necessary.

It is also preferred to use the carrier in processes for sealing with a resilient sealer, among others because such a sealer can easily be kept in a rest position with friction by slight compression, because such a sealer alone can be brought into at least a preliminary sealing sufficient for most manufacturing steps and because any capping thereof can be delayed to a late stage when the ampoules have been released from the carrier. As indicated earlier a preferred type of capping is the sleeve type, extending from front to rear, which can be applied for example after any isolated steps in the process.

The carriers can be used to achieve any of the advantages mentioned regardless of manufacturing plant characteristics. The carriers can for example be used to facilitate manual handling of ampoules in the various steps. But with advantage the carriers can be used in automated and mechanized plant layouts in which manipulation, transport and operations are conducted by designed machinery, wherein the carrier simplicity and flexibility can be optimally exploited.

For reasons set out the products manufactured according to the methods steps of the invented system have advantages as such and are part of the system in their own right.

SUMMARY OF DRAWINGS

FIGS. 5A to 5F show in plan view, short side view, long side view, section, partial enlargement and perspective view respectively an ampoule carrier according to the invention.

DESCRIPTION OF DRAWINGS

Figure 1:
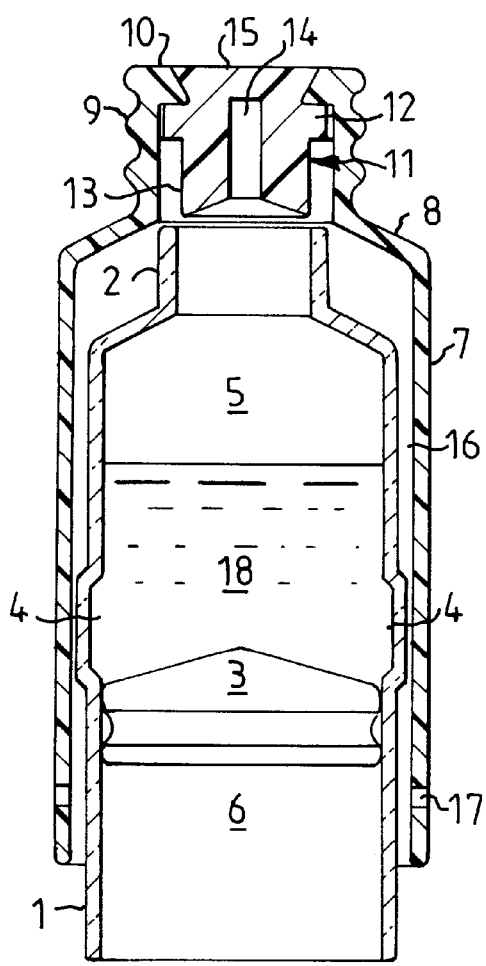
FIG. 1 shows a prior art dual chamber cartridge of the type having an external sleeve.

FIG. 1 shows a dual chamber cartridge having an external sleeve of the general type disclosed in the abovementioned U.S. Pat. No. 5,435,076 patent specification, incorporated herein by reference. The drawing illustrates a relationship between the parts before sealer and sleeve have been axially displaced to sealing engagement with the barrel opening and before a lyophilization step has taken place. A syringe barrel 1 has a neck 2 with a front opening. In barrel 1 a piston 3 is inserted to the rear of a bypass 4, dividing the barrel into a front chamber 5 and a rear chamber 6. Barrel 1 is surrounded by sleeve 7, having about the same length as the barrel. Front end 8 of the sleeve corresponds to neck 2 of the barrel and extends further into a portion 9, having external threads for the attachment of a needle holder, and ends in a inward flange 10. Inside portion 9 is arranged a stopper 11 with an outward flange 12. Sleeve inward flange 10 and stopper outward flange 12 are mutually adapted to prevent the stopper from moving forward relative the sleeve. The stopper further comprises a roughly cylindrical part 13, designed to sealingly enter the barrel opening, and a cavity 14 therein, creating a thinned membrane 15, for penetration by a needle. A spacing 16 is provided between sleeve and barrel to enable vapor from the opening escape to the rear during lyophilization. Attachment means 17 are arranged at the sleeve rear part allowing connection to actuating means and anchoring of the sleeve behind the barrel end. Front chamber 5 is initially filled with a solution 18 to be lyophilized into a dry state. Barrel opening is then closed by moving the sleeve 7 and stopper 11 axially rearwards. Finally (not shown) a solvent is filled into rear chamber 6, a rear piston is inserted to close rear chamber 6 and an actuating mechanism is attached to the rear end of the cartridge unit.

Figure 2:
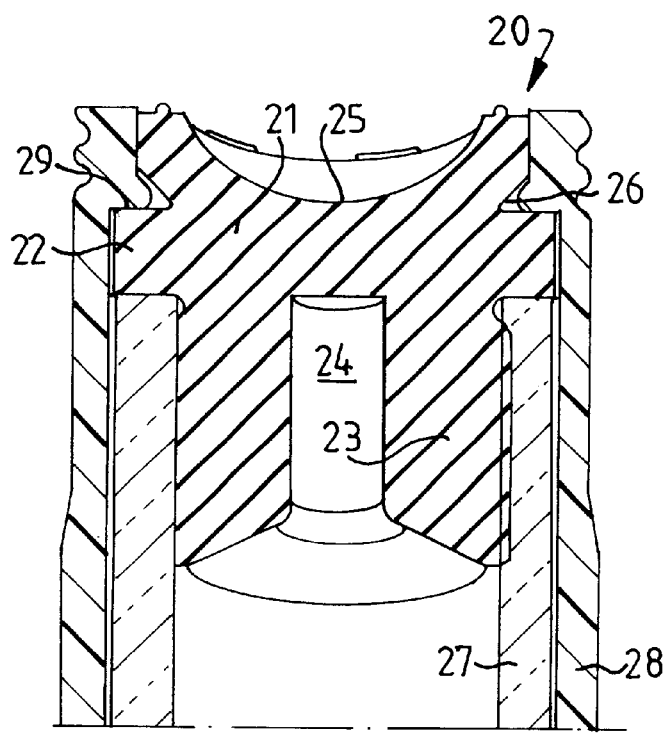
FIG. 2 shows the front end of an alternative cartridge design according to the invention.

FIG. 2 illustrates a preferred alternative design of a cartridge front end, which cartridge in other respects may be similar to the design shown in FIG. 1. The cartridge is generally designated 20 and comprises a stopper type sealer 21, having a flange 22, a roughly cylindrical part 23 for insertion into the barrel opening, a cavity 24 in the cylindrical part, an upper surface 25 shaped as a bowl and a recess 26 in front of flange 22. The cartridge further comprises a generally cylindrical barrel 27 and a sleeve 28 extending from the stopper front end to the barrel rear end and having an inward flange 29 for cooperation with the stopper flange 22 and recess 26. The stopper cylindrical part 23 is inserted into the barrel 27 front end, the opening of which is simply the termination of cylindrical barrel 27 and in this illustration forms a flat edge. Stopper flange 22 rests on barrel 27 flat opening edge but has a larger diameter than the cylindrical barrel so as to extend radially beyond the barrel outside dimensions and at least partially into the spacing between the barrel 27 and the sleeve 28. As also shown the flange has a larger diameter than any stopper structure in front of it so that the flange can be abutted by an axially rearward movement of an retention surface. Inward flange 29 of sleeve 28 is designed to form such a retention surface for abutment against stopper flange 22 and it is clear that inward flange 29 can be contacted with sleeve flange 22 by a rearward movement of the sleeve also after that the stopper has been inserted into the opening. Stopper recess 26 cooperates with an innermost bulge on sleeve inward flange 29 to create a weak snap-lock mechanism which does not prevent a rearward movement of sleeve 28 relative stopper 21. Stopper upper surface 25 bowl shape serves, in addition to cavity 24, to further limit the necessary penetration length for e.g. a sharp or needle through the central stopper part. The rear parts of cartridge 20 (not shown) can be designed as in FIG. 1, i.e. with an intermediate piston dividing the barrel into a front chamber and a rear chamber, a by-pass arrangement, a rear piston and an anchoring of the sleeve to barrel rear end, possibly integral with structures for a rear piston actuating mechanism. In accordance with the principles of the invention the design can with preference be used in a lyophilization step in which the stopper flange 22 is frictionally held above the barrel opening. This can be done without presence of the sleeve and the spacing between barrel 27 and sleeve 28 can be made for other considerations than providing a vapor conduit, as required in the prior art.

Figure 3A:
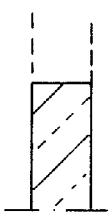
FIGS. 3A to 3D illustrates schematically, in cross-sections through a single barrel wall, various opening edge shapes discussed in connection with the invention.
Figure 3B:
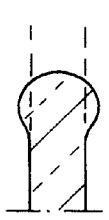
Figure 3C:
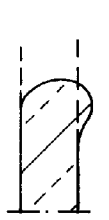
Figure 3D:
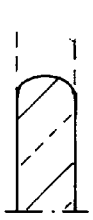

FIGS. 3A to 3D illustrates schematically, in axial cross-sections through a single ampoule wall, various opening edge shapes discussed in connection with the invention. In FIG. 3A the edge is rectangular in cross-section and forms a straight termination of the ampoule wall. This edge shape is not easily manufactured without debris formation and is not optimal in view of stopper insertion, safety and strength. FIG. 3B illustrates an edge having drop form in cross-section wherein drop dimensions lateral to ampoule axis are larger than ampoule wall thickness so that edge material extends both inside and outside ampoule wall nominal diameters. A drop form often results from liquid contraction after partial melting of edge material, for example when trimming or cutting a glass semi-manufacture. Although the rounded form as such is beneficial the drop material outside ampoule nominal wall thickness is not for reasons discussed. FIG. 3C illustrates a preferred edge form which is still rounded but at one side of the section, the left side in the Figure, no material is found radially outside the ampoule wall nominal wall surface. The wall surface without protruding material can be arranged on the ampoule outside or on the ampoule inside depending on which of the problems described are to be avoided. FIG. 3D illustrates a still more preferred edge profile which is rounded substantially in the form of a semi-circle with no material extending beyond the nominal wall thickness limitations on either side. With this design all the problems discussed can be avoided. The advantages are of greatest value for roughly cylindrical ampoules and when the opening has about the same diameter as the cylinder interior diameter. The preferred edge shapes are preferably used around the opening at the ampoule front end but with preference can also be used at other ampoule openings, such as the rear opening of a barrel type ampoule. In the Figures the nominal wall surfaces immediately below the edge zone are indicated by dotted lines.

Figure 4:
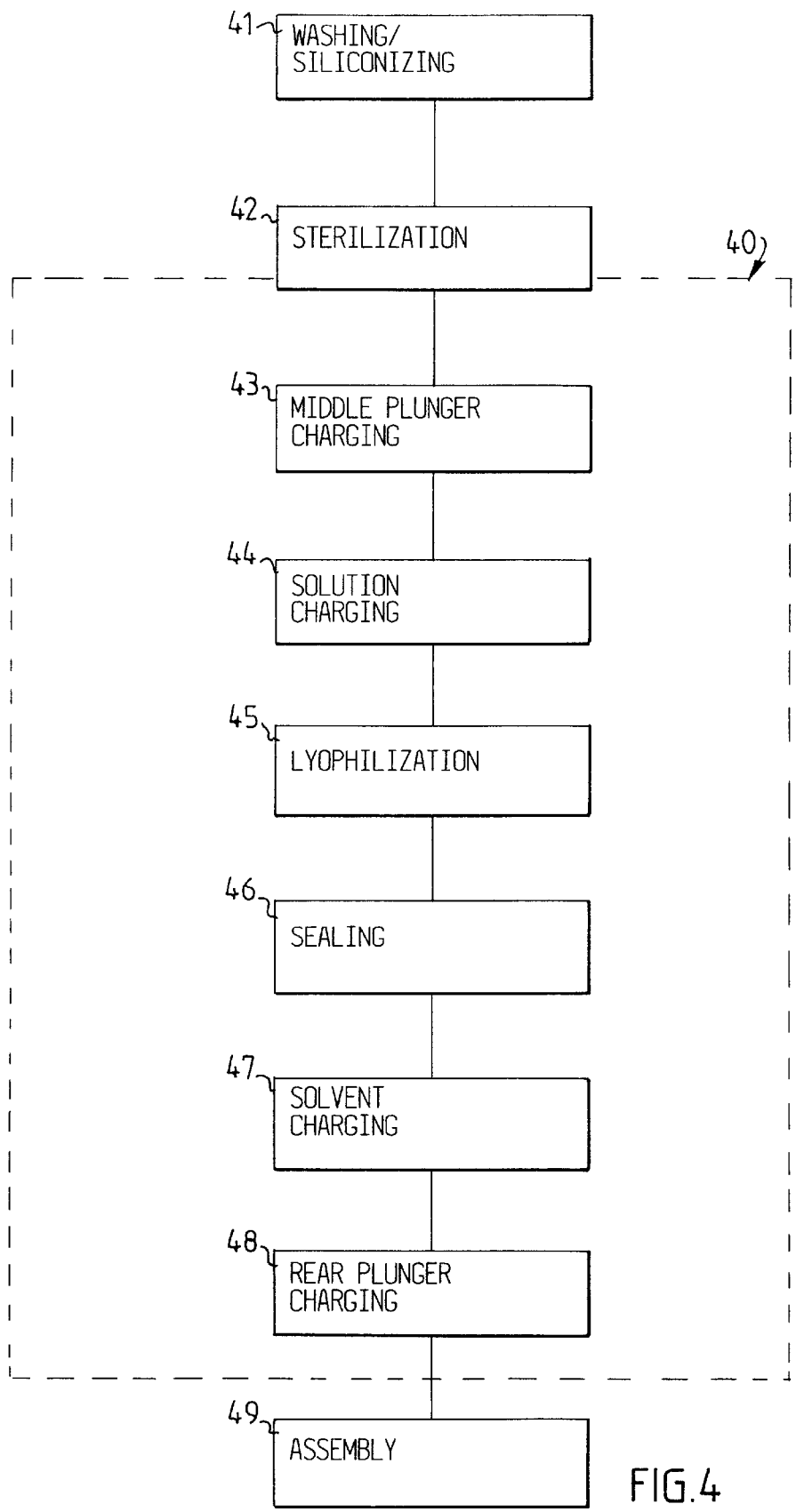
FIGS. 4 illustrates schematically the main steps in a procedure for manufacture of prefilled dual-chamber cartridges.

FIG. 4 illustrates schematically main steps in a preferred procedural sequence for manufacture of pre-filled dual-chamber syringe type cartridges. Several steps are conducted within a sterile zone, illustrated with dotted line 40. In a first step 41 syringe barrels are washed and siliconized. The so treated barrels are transmitted through a sterile oven 42 at the exit of which they enter the sterile zone 40. In a piston charging step 43 an intermediate piston is inserted into the barrel to delimit the front and the rear chambers. In charging step 44 the solution to be lyophilized is filled into the front chamber and the solution is lyophilized in step 45. Next 46 the barrel front end is sealed in-situ in the lyophilizing chamber. A solvent for the lyophilized powder is filled into the rear chamber in step 47. In step 48 a rear piston is inserted into the barrel rear end to confine the solvent in the rear chamber. The preparations in the barrel are now sealed from the surroundings and the prefilled barrel can leave the sterile zone 40. In a final assembly step 49, further components can be added, such as a sealer capping and rear actuating means, preferably by use of a sleeve as intermediate component as described. It is clear that all components charged into the barrel, notably the intermediate piston and the rear piston as well as the solution and the solvent, has to be sluiced into the sterile zone 40 in sterile condition.

In the above process it is preferred to use the ampoule carrier of the invention in all steps 43 to 48 performed within the sterile zone 40. Due to the carrier versatility it is also possible and preferred to use the carrier in the sterilization oven of step 42 and the carrier can be used in the washing and siliconizing step 41 although these steps can also be conducted with the ampoules in bulk or in blisters. It is generally preferred to remove the ampoules from the carrier before conducting the assembly steps 49. It is generally preferred to turn the ampoules with the carrier upside down between steps 46 and 47, and preferably this is the only turning step until ampoule removal from the carrier. In case the ampoules are of the preferred syringe type described all steps up to 46 inclusive can with preference be conducted form the upper side of the carrier. It is also possible to delay mounting of the sleeve until step 49 outside the sterile zone, which limits the number of components entered into that zone. According to the invention it is possible and preferred to charge the sealers into a carrier rest position, allowing vapor escape, which is preferably done between steps 44 and 45. The in-situ sealing of step 46 is preferably done by axially moving the charged sealers from the rest position into sealing engagement with barrel front opening.

Figure 5F:
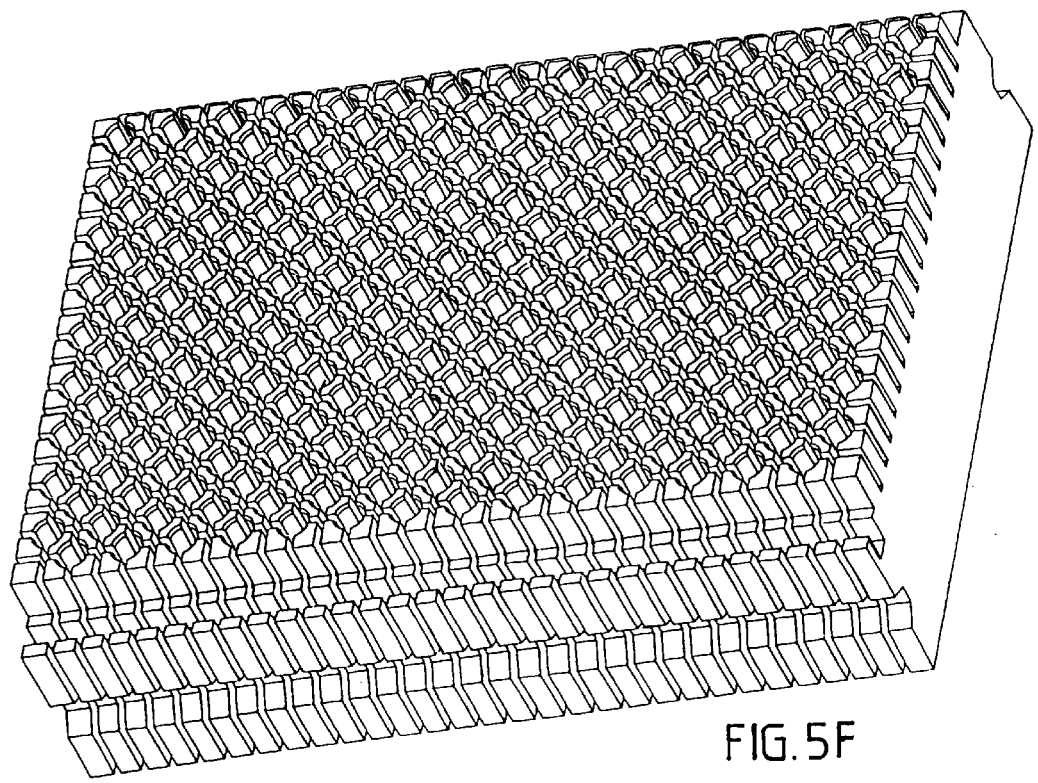

FIGS. 5A to 5E show in various views, section and enlargement an ampoule carrier body according to the invention. FIG. 5F shows on a slightly larger scale the carrier body in perspective view. The roughly rectangular carrier body 50 is a monolithic part preferably made from an aluminum block and has an upper or front side 51 and a lower or rear side 52. Numerous ampoule channels 53 are arranged in the form of 29 columns and 18 rows, which are interleaved to give 261 channels. As best seen in FIG. 5E the channels comprise a bore 531 in the carrier body 50, which bore is delimited by an inner wall 532 and the uppermost part 233 of which is slightly conical to facilitate ampoule and sealer insertion. In the body upper part 51 are arranged 29 linear guiding cut-outs 54, each passing through the upper parts of all channels in the column and, as best seen in FIGS. 5B and 5D, to only a partial depth of the channels. Cut-outs 54 act as guiding structures for an upper lock arrangement, to be further described in connection with FIG. 6, also used as a tool for moving sealers from a rest position to a sealing position. Similarly 18 linear vapor conduit cut-outs 55 are arranged at the body upper part 51, each cut-out passing through the upper parts of all channels in the row and, as best seen in FIGS. 5B and 5D, to only a partial depth of the channels. These vapor conduit cut-outs 55 serve as additional vapor escape routes during lyophilization when a sealer has been inserted into a rest position in the channel upper part. As best seen in FIGS. 5D and 5E lower locks are provided for each channel 53 at the block lower side 52 in the form of a shoulder 56, extending radially inwardly from the bore surface 532, on which shoulders a rim part of an ampoule is intended to rest. As best seen in FIG. 5C, the guiding cut-outs 54 extend down one of the long sides of the carrier body at side slits 57 and a trough 58 extends along the same body side transversal to the side slits, all for the purpose of supporting the combined lock and sealer pressing tool. Longitudinal recesses 59 are provided for the purpose of handling the carriers in a mechanized manufacturing plant. In use ampoules can be inserted from the upper part side 51 of the body into the channels to rest on lower lock surfaces 56. Sealers can be inserted from the same body side into a rest position located in the cut-out parts 54 or 55 of the channels and secured against withdrawal by the upper locks in a first axial position and can later be brought to sealing by moving the upper locks to a deeper second position.

Figure 6D:
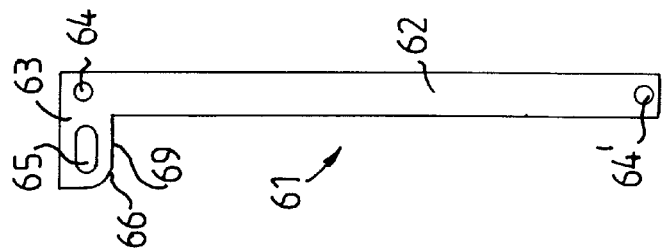
FIG. 6D shows an individual lock for a column of channels.
Figure 6B:
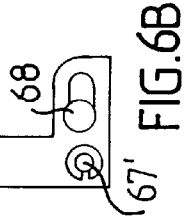
FIGS. 6A to 6C show in plan view and side views an upper lock arrangement for the ampoule carrier of FIG. 5.
Figure 6C:
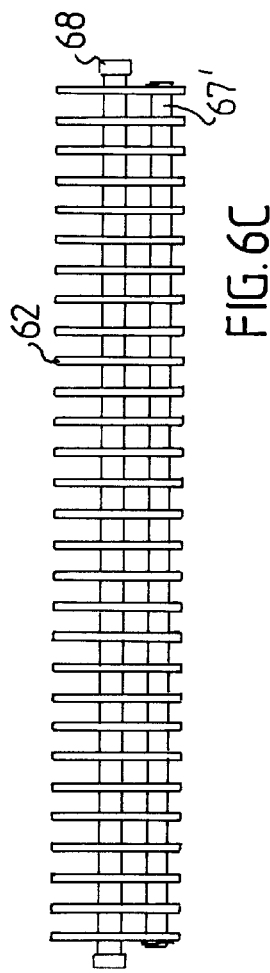
Figure 6A:
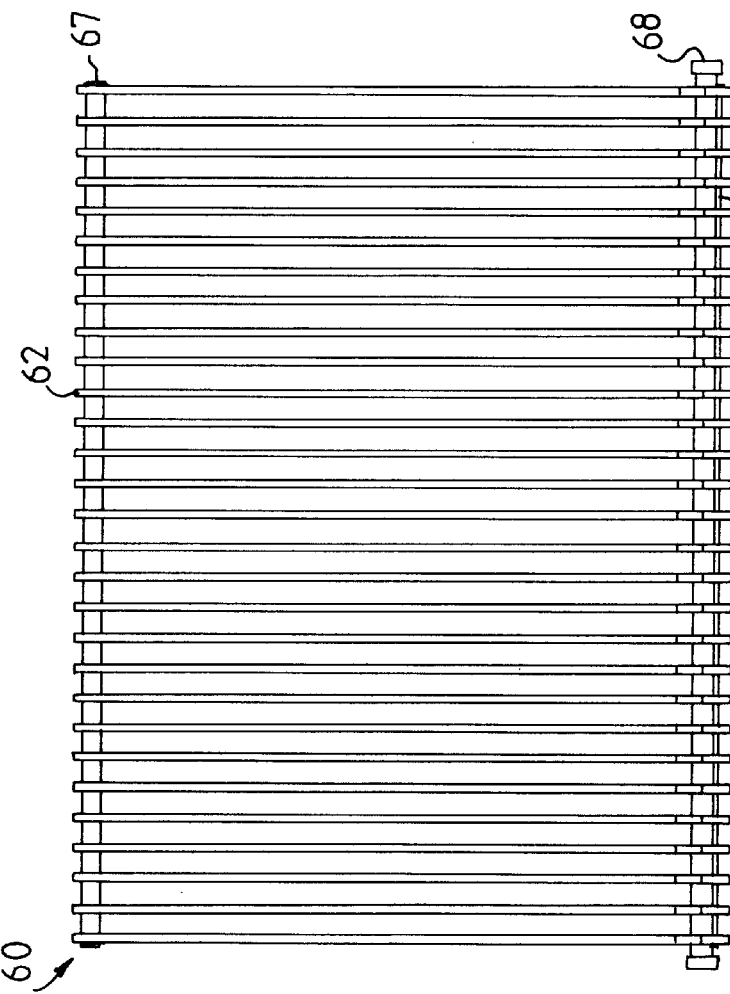

FIGS. 6A to 6C show in plan view and side views an upper lock arrangement 60 for the ampoule carrier of FIG. 5, wherein FIG. 5F is on about the same scale. FIG. 6D shows an individual lock 61 for a column of channels. As best seen in FIG. 6D an individual column lock is generally shaped as a band in L-form having a longer straight locking part 62 and a shorter hinge part 63. The column lock further comprises end holes 64 and 64' for joining several column locks 61 into a parallel arrangement and an elongated hinge hole 65, allowing a certain movement along the hinge part 63 when an axis is placed in hinge hole 65. The curvature radius 66 is centered on the most close part of hole 65 and the curvature continues into a straight portion 69 of the hinge part 63. As best seen in FIGS. 6A, 6B and 6C a unitary lock arrangement is formed from 29 column locks 61 placed in parallel and held together by rods 67 and 67', passing through holes 64 and 64' respectively. Hinge axis 68 passes through elongated hinge holes 65 of all column locks 61.

When combined with the carrier body of FIG. 5 hinge axis 68 is placed, and preferably secured, in trough 58 so that each hinge part 63 of the column locks 61 becomes located in a corresponding side slit 57. If each column lock 61 straight locking part 62 is inserted into its corresponding guiding cut-out 54 on the upper side 51 of carrier body 50, the whole lock arrangement 60 can be moved axially with respect to channels 53 to the extent allowed by elongated hinge hole 65. In particular this allows the lock arrangement 60 to occupy an uppermost position, still guided by guiding cut-outs 54, abutting stoppers in a rest position above ampoule openings, and a lowermost position, the movement to which position acts to press the sealers into sealing engagement with ampoule openings. In the uppermost position hinge axis 68 is centered with curvature 66 of hinge part 63 and the curvature 66 cooperates with bottom parts of side slits 57, compare FIG. 5D, to allow the lock arrangement 60 to be swung, around hinge axis 68, away from carrier body upper side 51. In the lowermost position, straight portion 69 of hinge part 63 cooperates with bottom parts of side slits 57 so as to prevent lock arrangement 60 from rotating around hinge axis 68 and preferably means (not shown) are provided to releasably secure the lock arrangement in this position.

Figure 7:
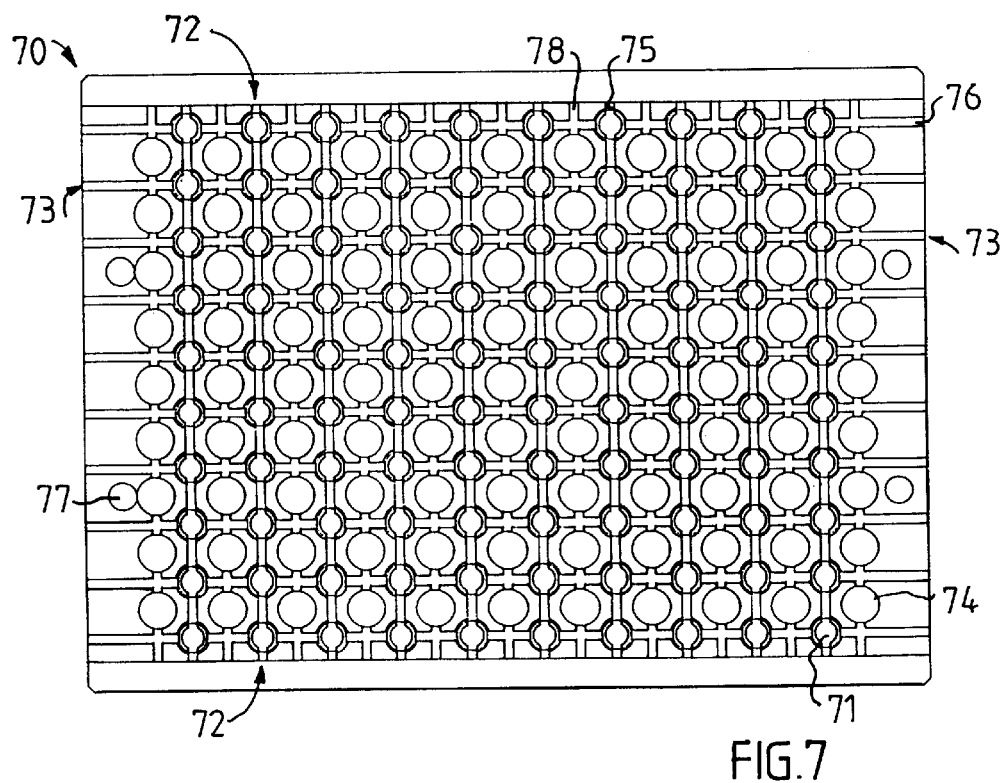
FIG. 7 shows in plan view an alternative ampoule carrier having another channel distribution.

FIG. 7 shows in plan view of the upper side another embodiment of an ampoule carrier body 70 according to the invention. The carrier body has generally the same features as the embodiment of FIG. 5 but with a slightly different channel layout. Channels 71 are organized into ten columns times ten rows 73, the latter having a slightly smaller spacing resulting in a generally rectangular layout. Between each column and row other columns and rows are inserted with plain holes 74, mainly serving to reduce carrier mass and to increase contact surface in heat exchange process steps, notably sterilization with hot gas. Channels 71 has the same features as described in relation to FIG. 5E. Similarly the carrier body 70 upper surface has guiding cut-outs 75, for a combined upper lock and pressing arrangement similar to that of FIG. 6. The carrier body also has transverse venting cut-outs 76, providing vapor escape routes during lyophilization. Cut-outs 75 and 76 penetrates only to a part of channel axial lengths. Holes 77 are handling assisting structures for the carriers in a mechanized plant. In this embodiment no hinges are provided for the upper lock arrangement. Instead ten straight column lock bands are united to form a plain grid. As in the embodiment of FIGS. 5 and 6 the grid can be positioned with the column locks in guiding cut-outs 75 above sealers in a rest position for later axial movement to bring the sealers into engagement with ampoule openings. The grid can, however, also be positioned in additional cut-outs 78, passing over holes 74, in order to expose holes 71, e.g. for filling procedure steps, and the grid will still be kept within the boundaries of the carrier body upper surface. Fixture means (not shown) can be provided to retain the grid in the various positions.

The invention is not limited to the embodiments described but can be varied within the scope of the patent claims.

What is claimed is:

1. A carrier/ampoule unit, for use in manufacture of prefilled ampoules, the unit comprising i) at least one ampoule and ii) a carrier having more than one ampoule seat, each seat providing a channel for axial insertion but radial retention of the ampoule, the ampoule comprising a) a container part with a front or upper end and a rear or lower end defining the ampoule axis therebetween, defining the radial directions perpendicular to the axis and defining an ampoule height, and b) an opening to the container part at least at the front end, wherein
    the channels are formed as cavities substantially in the form of bores in a carrier body part,
    the cavity walls have at least the same height along the ampoule axis as the ampoule height, and
    the cavity walls are substantially continuous around said axis and along said height.

2. The unit of claim 1, wherein the ampoule container part is selected from the group consisting of a tube, a vessel, a bag, a vial, a capsule, a carpoule, a syringe barrel and combinations thereof.

3. The unit of claim 2, wherein the container part is at least partly symmetrical with constant cross-section along a symmetry axis.

4. The unit of claim 3, wherein the container part is tube-shaped.

5. The unit of claim 1, wherein the ampoule comprises a syringe barrel having a front opening and a rear opening.

6. The unit of claim 5, wherein the ampoule is substantially cylindrical.

7. The unit of claim 5, wherein the barrel comprises dual or multi chambers having at least one valve or by-pass arrangement.

8. The unit of claim 1, wherein channel width is about the same as a largest width of the ampoule.

9. The unit of claim 1, wherein each channel cross-section profile is about congruent with a cross-section profile of the ampoule.

10. The unit of claim 1, wherein each channel has a length at least as long as the ampoule height.

11. The unit of claim 10, wherein channel is longer than the ampoule height.

12. The unit of claim 11, comprising a sealer arranged in each channel at the ampoule front end.

13. The unit of claim 12 wherein the sealer is frictionally held in the channel.

14. The unit of claim 1, wherein each seat further comprises at least one lock attached to the carrier and the lock is capable of restricting ampoule axial movement.

15. The unit of claim 14, wherein the lock has a surface extending in to the channel at an ampoule front and/or rear end.

16. The unit of claim 15, wherein the surface only partially covers the channel cross-section.

17. The unit of claim 16, wherein the surface only partially covers the ampoule end surface.

18. The unit of claim 14, wherein a single locking structure provides locking surfaces for more than one seat.

19. The unit of claim 18, wherein the locking structure comprises at least one bar or band spanning over more than one channel.

20. The unit of claim 14, wherein the lock is releasably attached to the carrier.

21. The unit of claim 14, wherein the at least one lock comprises two locks with a separation at least equal to the ampoule height.

22. The unit of claim 21, wherein the separation is larger than the ampoule height.

23. The unit of claim 22, wherein the ampoule and a sealer are arranged between the locks.

24. The unit of claim 1, comprising a tool arranged axially movable in relation to at least one channel and having a part able to enter the channel.

25. The unit of claim 24, wherein the tool is arranged at least at the carrier upper end.

26. The unit of claim 24, wherein the tool is used as a lock.

27. The unit of claim 24, wherein the tool includes a plurality of parts able to enter a plurality of channels upon axial movement of the tool.

28. The unit of claim 24, wherein the carrier includes guiding structures for the tool axial movement.

29. The unit of claim 28, wherein each channel is provided with individual guiding structures.

30. The unit of claim 28, wherein the guiding structures comprise a stop surface for the tool axial movement towards the channel.

31. The unit of claim 28, wherein the guiding structures comprise recesses in the carrier body.

32. The unit of claim 1, wherein the carrier comprises venting conduits at least between the ampoule front end and the carrier exterior.

33. The unit of claim 32, wherein the conduits are formed as recesses in the carrier body.

34. A carrier/ampoule unit, for use in manufacture of prefilled ampoules, the unit comprising i) at least one ampoule a)a container part with a front or upper end and a rear or lower end defining the ampoule axis therebetween, defining the radial directions perpendicular to the axis and defining an ampoule height, and b) an opening to the container part at least at the front end, ii) a carrier having more than one ampoule seat, each seat providing a channel for axial insertion but radial retention of the ampoule, wherein
    the channel length is longer than the ampoule height, and
    the channel part beyond the ampoule comprises an interior surface distributed around the channel circumference and has substantially the same cross-section profile as the channel part occupied by the ampoule, and
    iii) a sealer frictionally held to the interior surface in a non-sealing relationship to the opening of the ampoule.

35. The unit of claim 34, wherein the surface is generally tube shaped over at least an axial part.

36. The unit of claim 34, wherein the sealer is positioned above the front opening of the ampoule.

37. The unit of claim 34, wherein the ampoule container part is selected from the group consisting of a tube, a vessel, a bag, a vial, a capsule, a carpoule, a syringe barrel and combinations thereof.

38. The unit of claim 34, wherein the container part is at least partly symmetrical with constant cross-section along a symmetry axis.

39. The unit of claim 34, wherein the container part is tube-shaped.

40. The unit of claim 34, wherein the ampoule comprises a syringe barrel having a front opening and a rear opening.

41. The unit of claim 40, wherein the ampoule is substantially cylindrical.

42. The unit of claim 40, wherein the barrel comprises dual or multi chambers having at least one valve or by-pass arrangement.

43. The unit of claim 34, wherein each channel is formed as a bore in a carrier body part.

44. The unit of claim 34, wherein each channel width is about the same as a largest width of the ampoule.

45. The unit of claim 34, wherein each channel cross-section profile is about congruent with a cross-section profile of the ampoule.

46. The unit of claim 34, wherein each seat further comprises at least one lock attached to the carrier and the lock is capable of restricting ampoule axial movement.

47. The unit of claim 46, wherein the lock has a surface extending into the channel at an ampoule front and/or rear end.

48. The unit of claim 47, wherein the surface only partially covers the channel cross-section.

49. The unit of claim 48, wherein the surface only partially covers the ampoule end surface.

50. The unit of claim 46, wherein a single locking structure provides locking surfaces for more than one seat.

51. The unit of claim 50, wherein the locking structure comprises at least one bar or band spanning over more than one channel.

52. The unit of claim 46, wherein the lock is releasably attached to the carrier.

53. The unit of claim 46, wherein the at least one lock comprises two locks with a separation at least equal to the ampoule height.

54. The unit of claim 53, wherein the separation is larger than the ampoule height.

55. The unit of claim 54, wherein the ampoule and a sealer are arranged between the locks.

56. The unit of claim 34, comprising a tool arranged axially movable in relation to at least one channel and having a part able to enter the channel.

57. The unit of claim 56, wherein the tool is arranged at least at the carrier upper end.

58. The unit of claim 56, wherein the tool is used as a lock.

59. The unit of claim 56, wherein the tool includes a plurality of parts able to enter a plurality of channels upon axial movement of the tool.

60. The unit of claim 56, wherein the carrier includes guiding structures for the tool axial movement.

61. The unit of claim 60, wherein each channel is provided with individual guiding structures.

62. The unit of claim 60, wherein the guiding structures comprise a stop surface for the tool axial movement towards the channel.

63. The unit of claim 60, wherein the guiding structures comprise recesses in the carrier body.

64. The unit of claim 34, wherein the carrier comprises venting conduits at least between the ampoule front end and the carrier exterior.

65. The unit of claim 64, wherein the conduits are formed as recesses in the carrier body.

66. A carrier/ampoule unit, for use in manufacture of prefilled ampoules, the unit comprising i) at least one ampoule and ii) a carrier having more than one ampoule seat, each seat providing a channel for axial insertion but radial retention of the ampoule, the ampoule comprising a) a container part with a front or upper end and a rear or lower end defining the ampoule axis therebetween, defining the radial directions perpendicular to the axis and defining an ampoule height, and b) an opening to the container part at least at the front end, the unit further comprising a lower lock attached to the carrier adjacent each channel and having a surface extending at least partially into the channel, an upper lock attached to the carrier adjacent each channel and having a surface extending at least partially into the channel, the upper lock surface and the lower lock surface being axially separated with a distance at least corresponding to the ampoule height, at least one of the lower lock and the upper lock being releasably attached to the carrier adjacent each channel, and the lower lock surface and/or the upper lock surface only partially covering the channel cross-sections.

67. The unit of claim 66, wherein the lower lock and/or the upper lock are axially movably attached t o the channel.

68. The unit of claim 66, wherein the ampoule container part is selected from the group consisting of a tube, a vessel, a bag, a vial, a capsule, a carpoule, a syringe barrel and combinations thereof.

69. The unit of claim 68, wherein the container part is at least partly symmetrical with constant cross-section along a symmetry axis.

70. The unit of claim 68, wherein the container part is tube-shaped.

71. The unit of claim 66, wherein the ampoule comprises a syringe barrel having a front opening and a rear opening.

72. The unit of claim 71, wherein the ampoule is substantially cylindrical.

73. The unit of claim 71, wherein the barrel comprises dual or multi chambers having at least one valve or by-pass arrangement.

74. The unit of claim 66, wherein each channel is formed as a bore in a carrier body part.

75. The unit of claim 66, wherein each channel width is about the same as a largest width of the ampoule.

76. The unit of claim 66, wherein each channel cross-section profile is about congruent with a cross-section profile of the ampoule.

77. The unit of claim 66, wherein each channel is longer than the ampoule height.

78. The unit of claim 77, comprising a sealer arranged in each channel at the ampoule front end.

79. The unit of claim 78, wherein the sealer is frictionally held in the channel.

80. The unit of claim 66, wherein a single locking structure provides locking surfaces for more than one seat.

81. The unit of claim 80, wherein the locking structure comprises at least one bar or band spanning over more than one channel.

82. The unit of claim 66, wherein the separation is larger than the ampoule height.

83. The unit of claim 66, wherein the ampoule and a sealer are arranged between the locks.

84. The unit of claim 66, wherein the at least one of the lower lock and the upper lock is arranged axially movable in relation to at least one channel and having a part able to enter the channel.

85. The unit of claim 84, wherein the upper lock is arranged at least at the carrier upper end.

86. The unit of claim 84, wherein the at least one of the lower lock and the upper lock includes a plurality of parts able to enter a plurality of channels upon axial movement of the a one of the lower lock and the upper lock.

87. The unit of claim 84, wherein the carrier includes guiding structures for the lock axial movement.

88. The unit of claim 87, wherein each channel is provided with individual guiding structures.

89. The unit of claim 87, wherein the guiding structures comprise a stop surface for the lock axial movement towards the channel.

90. The unit of claim 87, wherein the guiding structures comprise recesses in the carrier body.

91. The unit of claim 66, wherein the carrier comprises venting conduits at least between the ampoule front end and the carrier exterior.

92. The unit of claim 91, wherein the conduits are formed as recesses in the carrier body.

93. A carrier/ampoule unit, for use in manufacture of prefilled ampoules, the unit comprising i) at least one ampoule and ii) a carrier having more than one ampoule seat, each seat providing a channel for axial insertion but radial retention of the ampoule, the ampoule comprising a) a container part with a front or upper end and a rear or lower end defining the ampoule axis therebetween, defining the radial directions perpendicular to the axis and defining an ampoule height, and b) an opening to the container part at least at the front end, the unit further comprising a lower lock attached to the carrier adjacent each channel and having a surface extending at least partially into the channel, an upper lock attached to the carrier adjacent each channel and having a surface extending at least partially into the channel, at least one of the lower lock and the upper lock being releasably attached to the carrier adjacent the channel and arranged to provide locking surfaces for more than one seat, and guiding structures for at least the releasable lock arranged on the carrier adjacent each channel.

94. The unit of claim 93, wherein at least the releasable lock is axially movable in relation to the channel.

95. The unit of claim 94, wherein the guiding structure s comprise at least a stop surface limiting movement of the movable upper lock or lower lock towards the channel.

96. The unit of claim 93, wherein the ampoule container part is selected from the group consisting of a tube, a vessel, a bag, a vial, a capsule, a carpoule, a syringe barrel and combinations thereof.

97. The unit of claim 96, wherein the container part is at least partly symmetrical with constant cross-section along a symmetry axis.

98. The unit of claim 96, wherein the container part is tube-shaped.

99. The unit of claim 93, wherein the ampoule comprises a syringe barrel having a front opening and a rear opening.

100. The unit of claim 99, wherein the ampoule is substantially cylindrical.

101. The unit of claim 99, wherein the barrel comprises dual or multi chambers having at least one valve or by-pass arrangement.

102. The unit of claim 93, wherein each channel is formed as a bore in a carrier body part.

103. The unit of claim 93, wherein each channel width is about the same as a largest width of the ampoule.

104. The unit of claim 93, wherein each channel cross-section profile is about congruent with a cross-section profile of the ampoule.

105. The unit of claim 93, wherein each channel has a length at least as long as the ampoule height.

106. The unit of claim 105, wherein each channel is longer than the ampoule height.

107. The unit of claim 106, comprising a sealer arranged in each channel at the ampoule front end.

108. The unit of claim 107, wherein the sealer is frictionally held in the channel.

109. The unit of claim 93, wherein the locking surfaces only partially cover the channel cross-section.

110. The unit of claim 109, wherein the surfaces only partially cover the ampoule end surface.

111. The unit of claim 93, wherein the lock arranged to provide the locking surfaces for more than one seat comprises at least one bar or band spanning over more than one channel.

112. The unit of claim 93, wherein the upper and lower locks have a separation at least equal to the ampoule height.

113. The unit of claim 112, wherein the separation is larger than the ampoule height.

114. The unit of claim 113, wherein the ampoule and a sealer are arranged between the locks.

115. The unit of claim 93, wherein the at least one of the lower lock and the upper lock is arranged axially movable in relation to at least one channel and having a part able to enter the channel.

116. The unit of claim 115, wherein the upper lock is arranged at least at the carrier upper end.

117. The unit of claim 115, wherein the at least one of the lower lock and the upper lock includes a plurality of parts able to enter a plurality of channels upon axial movement of the at least one of the lower lock and the upper lock.

118. The unit of claim 115, wherein the carrier includes guiding structures for the lock axial movement.

119. The unit of claim 118, wherein each channel is provided with individual guiding structures.

120. The unit of claim 118, wherein the guiding structures comprise a stop surface for the lock axial movement towards the channel.

121. The unit of claim 118, wherein the guiding structures comprise recesses in the carrier body.

122. The unit of claim 93, wherein the carrier comprises venting conduits at least between the ampoule front end and the carrier exterior.

123. The unit of claim 122, wherein the conduits are formed as reses in the carrier body.

124. A carrier/ampoule unit, for use in manufacture of prefilled ampoules, the unit comprising i) at least one ampoule, and ii) a carrier having one or several seats for an ampoule, the seat providing a channel for axial insertion but radial retention of the ampoule, the ampoule comprising a syringe barrel container part with a front or upper end and a rear or lower end defining the ampoule axis therebetween. defining the radial directions perpendicular to the axis and defining an ampoule height, the syringe barrel container part having a front opening and a rear opening wherein the channel is formed as a cavity, the cavity walls have at least the same height along the ampoule axis as the ampoule height, and the cavity walls are substantially continuous around said axis and along said height.

125. The unit of claim 124, wherein the ampoule is substantially cylindrical.

126. The unit of claim 124, wherein the barrel comprises dual or multi chambers having at least one valve or by-pass arrangement.

127. The unit of claim 124, wherein the container part is at least partly symmetrical with constant cross-section along a symmetry axis.

128. The unit of claim 127, wherein the container part is tube-shaped.

129. The unit of claim 124, wherein the cavity is formed as a bore in a carrier body part.

130. The unit of claim 124, wherein the channel width is about the same as a largest width of the ampoule.

131. The unit of claim 124, wherein the channel cross-section profile is about congruent with a cross-section profile of the ampoule.

132. The unit of claim 124, wherein the channel has a length at least as long as the ampoule height.

133. The unit of claim 132, wherein the channel is longer than the ampoule height.

134. The unit of claim 133, composing a sealer arranged in the channel at the ampoule front end.

135. The unit of claim 134, wherein the sealer is frictionally held in the channel.

136. The unit of claim 124, wherein the seat further comprises at least one lock attached to the carrier and the lock is capable of restricting ampoule axial movement.

137. The unit of claim 136, wherein the lock has a surface extending into the channel at an ampoule front and or rear end.

138. The unit of claim 137, wherein the surface only partially covers the channel cross-section.

139. The unit of claim 138, wherein the surface only partially covers the ampoule end surface.

140. The unit of claim 136, wherein a single locking structure provides locking surfaces for more than one seat.

141. The unit of claim 140, wherein the locking structure comprises at least one bar or band spanning over more than one channel.

142. The unit of claim 136, wherein the lock is releasably attached to the carrier.

143. The unit of claim 136, wherein the at least one lock comprises two locks with a separation at least equal to the ampoule height.

144. The unit of claim 143, wherein the separation is larger than the ampoule height.

145. The unit of claim 144, wherein the ampoule and a sealer arrranged between the locks.

146. The unit of claim 124, comprising a tool arranged axially movable in relation to at least one channel and having a part able to enter the channel.

147. The unit of claim 146, wherein the tool is arranged at least at the carrier upper end.

148. The unit of claim 146, wherein the tool is used as a lock.

149. The unit of claim 146, wherein the tool includes a plurality of parts able to enter a plurality of channels upon axial movement of the tool.

150. The unit of claim 146, wherein the carrier includes guiding structures for the tool axial movement.

151. The unit of claim 150, wherein each channel is provided with individual guiding structures.

152. The unit of claim 150, wherein the guiding structures comprise a stop surface for the tool axial movement towards the channel.

153. The unit of claim 150, wherein the guiding structures comprise recesses in the carrier body.

154. The unit of claim 124, wherein the carrier comprises venting conduits at least between the ampoule front end and the carrier exterior.

155. The unit of claim 154, wherein the conduits are formed as recesses in the carrier body.

156. A carrier/ampoule unit, for use in manufacture of prefilled ampoules, the unit comprising i) at least one ampoule, and ii) a carrier having one or several seats for an ampoule, the seat providing a channel for axial insertion but radial retention of the ampoule,the ampoule comprising a) a container part with a front or upper end and a rear or lower end defining the ampoule axis therebetween, defining the radial direction perpendicular to the axis and defining an ampoule height, and b) an opening to the container part at least at the front end, wherein the channel is formed as a cavity, the cavity walls have at least the same height along the ampoule axis as the ampoule height, the cavity walls are substantially continuous around said axis and along said height, and the seat comprises at least one attached to the carrier, the lock has a surface extending into the channel at the ampoule front end and/or the ampoule rear end and only partially covering the channel cross-section, and wherein the lock is capable of restricting ampoule axial movement.

157. The unit of claim 156, wherein the surface only partially covers the ampoule end surface.

158. The unit of claim 156, wherein the ampoule container part is selected from the group consisting of a tube, a vessel, a bag, a vial, a capsule, a carpoule, a syringe barrel and combinations thereof.

159. The unit of claim 158, wherein the container part is it least partly symmetrical with constant cross-section along a symmetry axis.

160. The unit of claim 159, wherein the container part is tube-shaped.

161. The unit of claim 156, wherein the ampoule comprises a syringe barrel having a front opening and a rear opening.

162. The unit of claim 161, wherein the ampoule is substantially cylindrical.

163. The unit of claim 161, wherein the barrel comprises dual or multi chambers having at least one valve or by-pass arrangement.

164. The unit of claim 156, wherein the cavity is formed as a bore in a carrier body part.

165. The unit of claim 156, wherein the channel width is about the same as a largest width of the ampoule.

166. The unit of claim 156, wherein the channel cross,-section profile is about congruent with a cross-section profile of the ampoule.

167. The unit of claim 156, wherein the channel has a length at least as long as the ampoule height.

168. The unit of claim 167, wherein the channel is longer than the ampoule height.

169. The unit of claim 168, comprising a sealer arranged in the channel at the ampoule front end.

170. The unit of claim 169, wherein the sealer is frictionally held in the channel.

171. The unit of claim 156, wherein a single locking structure provides locking surfaces for more than one seat.

172. The unit of claim 171, wherein the locking structure comprises at least one bar or band spanning over more than one channel.

173. The unit of claim 156, wherein the lock is releasably attached to the carrier.

174. The unit of claim 156, wherein the at least one lock comprises two locks with a separation at least equal to the ampoule height.

175. The unit of claim 174, wherein the separation is larger than the ampoule height.

176. The unit of claim 175, wherein the ampoule and a sealer are arranged between the locks.

177. The unit of claim 156, wherein the lock is arranged axially movable in relation to at least one channel and having a part able to enter the channel.

178. The unit of claim 177, wherein the lock is arranged at least at the carrier upper end.

179. The unit of claim 177, wherein the lock includes a plurality of parts able to enter a plurality of channels upon axial movement of the lock.

180. The unit of claim 177, wherein the carrier includes guiding structures for the lock axial movement.

181. The unit of claim 180, wherein each channel is provided with individual guiding structures.

182. The unit of claim 180, wherein the guiding structures comprise a stop surface for the lock axial movement towards the channel.

183. The unit of claim 180, wherein the guiding structures comprise recesses in the carrier body.

184. The unit of claim 156, wherein the carrier comprises venting conduits at least between the ampoule front end and the carrier exterior.

185. The unit of claim 184, wherein the conduits are formed as recesses in the carrier body.

186. A carrier/ampoule unit, for use in manufacture of prefilled ampoules, the unit comprising i) at least one ampoule and ii) a carrier having one or several seats for an ampoule, the seat providing a channel for axial insertion but radial retention of the ampoule, the ampoule comprising a) a container part with a front or upper end and a. Rear or lower end defining the ampoule axis therebetween, defining the radial directions perpendicular to the axis and defining an ampoule height, and b) an opening to the container part at least at the front end, wherein
the channel is formed as a cavity,
the cavity walls have at least the same height along the ampoule axis as the ampoule height,
the cavity walls arc substantially continuous around said axis and along said height, and
the seat comprises at least one lock attached to the carrier, and the lock is capable of restricting ampoule axial movement and provides locking surfaces for more than one seat.

187. The unit of claim 186, wherein the locking structure comprises at least one bar or band spanning over more than one channel.

188. The unit of claim 186, wherein the ampoule container part is selected from the group consisting of a tube, a vessel, a bag, a vial, a capsule, a carpoule, a syringe barrel and combinations thereof.

189. The unit of claim 188, wherein the container part is at least partly symmetrical with constant cross-section along a symmetry axis.

190. The unit of claim 189, wherein the container part is tube-shaped.

191. The unit of claim 186, wherein the ampoule comprises a syringe barrel having a front opening and a rear opening.

192. The unit of claim 191, wherein the ampoule is substantially cylindrical.

193. The unit of claim 191, wherein the barrel comprises dual or multi chambers having at least one valve or by-pass arrangement.

194. The unit of claim 186, wherein the cavity is formed as a bore in a carrier body part.

195. The unit of claim 186, wherein the channel width is about the same as a largest width of the ampoule.

196. The unit of claim 186, wherein the channel cross-section profile is about congruent with a cross-section profile of the ampoule.

197. The unit of claim 186, wherein the channel has a length at least as lone as the ampoule height.

198. The unit of claim 197, wherein the channel is longer than the ampoule height.

199. The unit of claim 198, comprising a sealer arranged in the channel at the ampoule front end.

200. The unit of claim 199, wherein the sealer is frictionally held in the channel.

201. The unit of claim 186, wherein the lock has a surface extending into the channel at an ampoule front and/or rear end.

202. The unit of claim 201, wherein the surface only partially covers the channel cross-section.

203. The unit of claim 202, wherein the surface only partially covers the ampoule end surface.

204. The unit of claim 186, wherein the lock is releasably attached to the carrier.

205. The unit of claim 186, wherein the at least one lock comprises two locks with a separation at least equal to the ampoule height.

206. The unit of claim 205, wherein the separation is larger than the ampoule height.

207. The unit of claim 206, wherein the ampoule and a sealer are arranged between the locks.

208. The unit of claim 186, wherein the lock is a=ranged axially movable in relation to at least one channel and having a part able to enter the channel.

209. The uit of claim 208, wherein the lock is arranged at least at the carrier upper end.

210. The unit of claim 208, wherein the lock includes a plurality of parts able to enter a plurality of channels upon axial movement of the lock.

211. The unit of claim 208, wherein the carrier includes guiding structures for the lock axial movement.

212. The unit of claim 211, wherein each channel is provided with individual guiding structures.

213. The unit of claim 211, wherein the guiding structures comprise a stop surface for the lock axial movement towards the channel.

214. The unit of claim 211, whcrcin the guiding structures comprise reccsses in the carrier body.

215. The unit of claim 186, wherein the carrier comprises venting conduits at least between the ampoule front end and the carrier exterior.

216. The unit of claim 215, wherein the conduits are formed as recesses in the carrier body.

217. A carrier/ampoule unit, for use in manufacture of prefilled ampoules, the unit comprising i) at least one ampoule, and ii) a carrier having one or several seats for an ampoule, the seat providing a channel for axial insertion but radial retention of the ampoule, the ampoule comprising a) a container part with a front or upper end and a rear or lower end defining the ampoule axis therebetween, defining the radial directions perpendicular to the axis and defining an ampoule height, and b) an opening to the container part at least at the front end, wherein
the channel is formed as a cavity,
the cavity walls have at least the same height along the ampoule axis as the ampoule height,
the cavity walls arm substantially continuous around said axis and along said height, and the seat comprises two locks attached to the carrier and capable of restricting ampoule axial movement, the two locks being separated by a distance at least equal to the ampoule height.

218. The unit of claim 217, wherein the separation distance is larger than the ampoule height.

219. The unit of claim 218, wherein the ampoule and a sealer are arranged between the locks.

220. The unit of claim 217, wherein the ampoule container part is selected from the group consisting of a tube, a vessel, a bag, a vial, a capsule, a carpoule, a syringe barrel and combinations thereof.

221. The unit of claim 220, wherein the container part is at least partly symmetrical with constant cross-section along a symmetry axis.

222. The unit of claim 221, wherein the container part is tube-shaped.

223. The unit of claim 217, wherein the ampoule comprises a syringe barrel having a front opening and a rear opening.

224. The unit of claim 223, wherein the ampoule is substantially cylindrical.

225. The unit of claim 223, wherein the barrel comprises dual or multi chambers having at least one valve or by-pass arrangement.

226. The unit of claim 217, wherein the cavity is formed as a bore in a carrier body part.

227. The unit of claim 217, wherein the channel width is about the same as a largest width of the ampoule.

228. The unit of claim 217, wherein the channel cross-section profile is about congruent with a cross-section profile of the ampoule.

229. The unit of claim 217, wherein the channel has a length at least as long as the ampoule height.

230. The unit of claim 229, wherein the channel is longer than the ampoule height.

231. The unit of claim 230, comprising a sealer arranged in the channel at the ampoule front end.

232. The unit of claim 231, wherein the sealer is frictionally held in the channel.

233. The unit of claim 217, wherein each of the locks has a surface extending into the channel at a corresponding one of an ampoule front and rear ends.

234. The unit of claim 233, wherein each of the surfaces only partially covers the channel cross-section.

235. The unit of claim 234 wherein each of the surfaces only partially covers a corresponding one of the ampoule end surfaces.

236. The unit of claim 217, wherein a single locking structure provides locking surfaces for more than one seat.

237. The unit of claim 236, wherein the locking structure comprises at least one bar or band spanning over more than one channel.

238. The unit of claim 217, wherein one of the locks is releasably attached to the carrier.

239. The unit of claim 217, wherein a first one of the locks is arranged axially movable in relation to at least one channel and having a part able to enter the channel.

240. The unit of claim 239, wherein the first lock is arranged at the carrier upper end.

241. The unit of claim 239, wherein the first lock includes a plurality of parts able to enter a plurality of channels at the axial movement.

242. The unit of claim 239, wherein the carrier includes guiding structures for the first lock axial movement.

243. The unit of claim 242, wherein each channel is provided with individual guiding structures.

244. The unit of claim 242, wherein the guiding structures comprise a stop surface for the first lock axial movement towards the channel.

245. The unit of claim 242, wherein the guiding structures comprise recesses in the carrier body.

246. The unit of claim 217, wherein the carrier comprises venting conduits at least between the ampoule front end and the carrier exterior.

247. The unit of claim 246, wherein the conduits are formed as recesses in the carrier body.

248. A carrier/ampoule unit, for use in manufacture of prefilled ampoules, the unit comprising i) at least one ampoule and ii) a carrier having one or several seats for an ampoule, the seat providing a channel for axial insertion but radial retention of the ampoule, the ampoule comprising a) a container part with a front or upper end and a rear or lower end defining the ampoule axis therebetween, defining the radial directions perpendicular to the axis and defining an ampoule height and b) an opening to the container part at least at the front end, the unit further comprising:

a lower lock attached to the carrier adjacent the channel and having a surface extending at least partially into the channel, an upper lock attached to the carrier adjacent the channel and having a surface extending at least partially into the channel, the upper lock surface and the lower lock surface being axially separated with a distance at least corresponding to the ampoule height and at least one of the lower lock and the upper lock being releasably attached to the carrier adjacent the channel, and wherein the lower lock and/or the upper lock are axially movably attached to the carrier adjacent the channel.

249. The unit of claim 248, wherein the ampoule container part is selected from the group consisting of a tube, a vessel, a bag, a vial, a capsule, a carpoule, a syringe barrel and combinations thereof.

250. The unit of claim 249, wherein the container part is at least partly symmetrical with constant cross-section along a symmetry axis.

251. The unit of claim 249, wherein the container part is tube-shaped.

252. The unit of claim 248, wherein the ampoule comprises a syringe barrel having a front opening and a rear opening.

253. The unit of claim 252, wherein the ampoule is substantially cylindrical.

254. The unit of claim 252, wherein the barrel comprises dual or multi chambers having at least one valve or by-pass arrangement.

255. The unit of claim 248, wherein the channel is formed as a bore in a carrier body part.

256. The unit of claim 248, wherein the channel width is about the same as a largest width of the ampoule.

257. The unit of claim 248, wherein the channel cross-section profile is about congruent with a cross-section profile of the ampoule.

258. The unit of claim 248, wherein the channel is longer than the ampoule height.

259. The unit of claim 258, comprising a sealer arranged in the channel at the ampoule front end.

260. The unit of claim 259, wherein the sealer is frictionally held in the channel.

261. The unit of claim 248, wherein a single locking structure provides locking surfaces for more than one seat.

262. The unit of claim 261, wherein the locking structure comprises at least one bar or band spanning over more than one channel.

263. The unit of claim 248, wherein the separation is larger than the ampoule height.

264. The unit of claim 248, wherein the ampoule and a sealer are arranged between the locks.

265. The unit of claim 248, wherein the at least one of the lower lock and the upper lock is arranged axially movable in relation to at least one channel and having a part able to enter the channel.

266. The unit of claim 265, wherein the upper lock is arranged at least at the carrier upper end.

267. The unit of claim 265, wherein the at least one of the lower lock and the upper lock includes a plurality of parts able to enter a plurality of channels upon axial movement of the at least one of the lower lock and the upper lock.

268. The unit of claim 265, wherein tie carrier includes guiding structures for the lock axial movement.

269. The unit of claim 268, wherein each channel is provided with individual guiding structures.

270. The unit of claim 268, wherein the guiding structures comprise a stop surface for the lock axial movement towards the channel.

271. The unit of claim 268, wherein the guiding structures comprise recesses in the carrier body.

272. The unit of claim 248, wherein the carrier comprises venting conduits at least between the ampoule front end and the carrier exterior.

273. The unit of claim 272, wherein the conduits &e formed as recesses in the carrier body.

* * * * *

UNITED STATES PATENT AND TRADEMARK OFFICE
CERTIFICATE OF CORRECTION

PATENT NO.    : 6,290,680 B1
DATED         : September 18, 2001
INVENTOR(S)   : Mikael Forsberg et al.

It is certified that error appears in the above-identified patent and that said Letters Patent is hereby corrected as shown below:

Column 21,
Line 40, after "wherein" insert -- each --.
Line 47, after "wherein" insert -- each --.
Line 57, change "in to" to -- into --.

Column 22,
Line 35, after "ampoule" insert -- comprising --.

Column 24,
Line 63, change "a" to -- at least --.

Column 25,
Line 34, change "structure s" to -- structures --.

Column 26,
Line 38, change "reses" to -- recesses --.

Column 27,
Line 8, change "composing" to -- comprising --.

Column 28,
Line 36, change "cross,-" to -- cross- --.

Column 29,
Line 19, change "a. Rear" to -- a rear --.
Line 61, change "lone" to -- long --.

Column 30,
Line 17, change "a=ranged" to -- arranged --.
Line 32, change "whcrcin" to -- wherein --;
Line 33, change "reccsses" to -- recesses --.

Column 31,
Line 28, change "ends." to -- end. --.

UNITED STATES PATENT AND TRADEMARK OFFICE
CERTIFICATE OF CORRECTION

PATENT NO. : 6,290,680 B1
DATED : September 18, 2001
INVENTOR(S) : Mikael Forsberg et al.

It is certified that error appears in the above-identified patent and that said Letters Patent is hereby corrected as shown below:

<u>Column 33,</u>
Line 7, change "tie" to -- the --.

<u>Column 34,</u>
Line 9, change "&e" to -- are --.

Signed and Sealed this

Sixteenth Day of July, 2002

Attest:

JAMES E. ROGAN
Attesting Officer      Director of the United States Patent and Trademark Office

UNITED STATES PATENT AND TRADEMARK OFFICE
CERTIFICATE OF CORRECTION

PATENT NO. : 6,290,680 B1
DATED : September 18, 2001
INVENTOR(S) : Mikael Forsberg et al.

It is certified that error appears in the above-identified patent and that said Letters Patent is hereby corrected as shown below:

<u>Column 26,</u>
Line 45, change "therebetween." to -- therebetween, --.

Signed and Sealed this

Third Day of December, 2002

JAMES E. ROGAN
*Director of the United States Patent and Trademark Office*